US009381114B2

(12) United States Patent
Underwood et al.

(10) Patent No.: US 9,381,114 B2
(45) Date of Patent: Jul. 5, 2016

(54) VITRECTOMY PROBE WITH ADJUSTABLE CUTTER PORT SIZE

(71) Applicant: Alcon Research, Ltd., Fort Worth, TX (US)

(72) Inventors: John R. Underwood, Laguna Nigel, CA (US); Jack Robert Auld, Laguna Nigel, CA (US); John Christopher Huculak, Mission Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 110 days.

(21) Appl. No.: 14/269,749

(22) Filed: May 5, 2014

(65) Prior Publication Data

US 2014/0364886 A1    Dec. 11, 2014

Related U.S. Application Data

(60) Division of application No. 13/219,017, filed on Aug. 26, 2011, now Pat. No. 8,844,566, which is a continuation of application No. 12/974,722, filed on Dec. 21, 2010, now Pat. No. 8,888,802.

(51) Int. Cl.
| | | |
|---|---|---|
| *A61F 9/007* | (2006.01) | |
| *A61B 17/32* | (2006.01) | |
| *A61B 17/3207* | (2006.01) | |
| *A61B 17/00* | (2006.01) | |

(52) U.S. Cl.
CPC ....... *A61F 9/00763* (2013.01); *A61B 17/32002* (2013.01); *A61B 17/320783* (2013.01); *A61B 2017/00402* (2013.01); *A61B 2017/320028* (2013.01); *A61B 2217/005* (2013.01); *Y10T 137/86839* (2015.04); *Y10T 137/87217* (2015.04); *Y10T 137/87233* (2015.04)

(58) Field of Classification Search
CPC ............... A61F 9/00763; A61B 17/320783; A61B 17/32002; A61B 2217/005; A61B 2017/320028; A61B 2017/00402; Y10T 137/87217; Y10T 137/86839; Y10T 137/87233
See application file for complete search history.

(56) References Cited

U.S. PATENT DOCUMENTS

| | | | |
|---|---|---|---|
| 2,196,927 | A | 4/1940 | Larson |
| 2,564,445 | A | 8/1951 | Parsons |
| 3,569,753 | A | 3/1971 | Babikyan |
| 3,884,238 | A | 5/1975 | O'Malley et al. |
| 4,005,734 | A | 2/1977 | Kubik |
| 4,210,146 | A | 7/1980 | Banko |
| 4,246,902 | A | 1/1981 | Martinez |
| 4,481,768 | A | 11/1984 | Goshorn et al. |

(Continued)

OTHER PUBLICATIONS

International Search Report and Written Opinion of the International Searching Authority, International Application No. PCT/2011/062797, dated Mar. 9, 2012, 10 pages.

(Continued)

*Primary Examiner* — Ryan J Severson
*Assistant Examiner* — Rachel S Papeika
(74) *Attorney, Agent, or Firm* — Darien Reddick

(57) ABSTRACT

Vitrectomy probes and system related thereto are disclosed herein. The disclosure describes various example vitrectomy probes having an adjustable cutting port size. Various example features are described for adjusting the size of the cutting port. Further, the disclosure provides examples for adjusting the size of the cutter port while the vitrectomy probe is in operation.

7 Claims, 13 Drawing Sheets

(56) References Cited

U.S. PATENT DOCUMENTS

| | | | |
|---|---|---|---|
| 4,489,724 A | 12/1984 | Arnegger |
| 4,548,205 A | 10/1985 | Armeniades |
| 4,589,414 A | 5/1986 | Yoshida et al. |
| 4,674,502 A | 6/1987 | Imonti |
| 4,696,298 A | 9/1987 | Higgins et al. |
| 4,768,506 A | 9/1988 | Parker et al. |
| 4,909,249 A | 3/1990 | Akkas et al. |
| 4,940,468 A | 7/1990 | Petillo |
| 4,986,827 A | 1/1991 | Akkas et al. |
| 4,989,614 A | 2/1991 | Dejter et al. |
| 5,019,035 A | 5/1991 | Missirlian et al. |
| 5,020,535 A | 6/1991 | Parker et al. |
| 5,047,008 A | 9/1991 | De Juan, Jr. et al. |
| 5,059,204 A | 10/1991 | Lawson et al. |
| 5,314,440 A | 5/1994 | Shapiro |
| 5,350,355 A | 9/1994 | Sklar |
| 5,350,390 A | 9/1994 | Sher |
| 5,547,473 A | 8/1996 | Peyman |
| 5,562,691 A | 10/1996 | Tano et al. |
| 5,626,595 A | 5/1997 | Sklar et al. |
| 5,632,758 A | 5/1997 | Sklar |
| 5,649,547 A | 7/1997 | Ritchart et al. |
| 5,669,923 A | 9/1997 | Gordon |
| 5,722,980 A | 3/1998 | Schulz et al. |
| 5,759,153 A | 6/1998 | Webler et al. |
| 5,843,111 A | 12/1998 | Vijfvinkel |
| 5,873,885 A | 2/1999 | Weidenbenner |
| 5,910,110 A | 6/1999 | Bastable |
| 6,010,496 A | 1/2000 | Appelbaum et al. |
| 6,165,136 A | 12/2000 | Nishtala |
| 6,176,865 B1 | 1/2001 | Mauze et al. |
| 6,261,241 B1 | 7/2001 | Burbank et al. |
| 6,485,499 B1 | 11/2002 | Oberkamp et al. |
| 6,514,268 B2 | 2/2003 | Finlay et al. |
| 6,527,736 B1 | 3/2003 | Attinger et al. |
| 6,629,986 B1 | 10/2003 | Ross et al. |
| 6,689,071 B2 | 2/2004 | Burbank et al. |
| 6,749,576 B2 | 6/2004 | Bauer |
| 6,773,445 B2 | 8/2004 | Finlay et al. |
| 7,025,732 B2 | 4/2006 | Thompson et al. |
| 7,517,322 B2 | 4/2009 | Weikel, Jr. et al. |
| 7,717,861 B2 | 5/2010 | Weikel et al. |
| 7,785,321 B2 | 8/2010 | Baerveldt |
| 8,038,692 B2 | 10/2011 | Valencia et al. |
| 8,187,293 B2 | 5/2012 | Kirchhevel |
| 2002/0026869 A1 | 3/2002 | Morita et al. |
| 2002/0124893 A1 | 9/2002 | Frank et al. |
| 2002/0173814 A1 | 11/2002 | Jung et al. |
| 2003/0078609 A1 | 4/2003 | Finlay et al. |
| 2003/0145721 A1 | 8/2003 | Oka et al. |
| 2003/0159738 A1 | 8/2003 | Lee |
| 2004/0049217 A1 | 3/2004 | Ross et al. |
| 2004/0138687 A1 | 7/2004 | Himes |
| 2004/0204732 A1 | 10/2004 | Muchnik |
| 2004/0211476 A1 | 10/2004 | Hager |
| 2005/0065453 A1 | 3/2005 | Shabaz et al. |
| 2005/0080441 A1 | 4/2005 | Dodge et al. |
| 2006/0167377 A1 | 7/2006 | Ritchart et al. |
| 2006/0167378 A1 | 7/2006 | Miller |
| 2006/0200040 A1 | 9/2006 | Weikel, Jr. et al. |
| 2007/0135752 A1 | 6/2007 | Domash et al. |
| 2007/0185512 A1 | 8/2007 | Kirchhevel |
| 2007/0185514 A1 | 8/2007 | Kirchhevel |
| 2008/0114264 A1 | 5/2008 | Weikel, Jr. et al. |
| 2008/0168985 A1 | 7/2008 | Turner et al. |
| 2008/0172078 A1 | 7/2008 | Svetic |
| 2009/0048533 A1 | 2/2009 | Miller |
| 2009/0088784 A1 | 4/2009 | DeBoer et al. |
| 2009/0157111 A1 | 6/2009 | Goh et al. |
| 2009/0234274 A1 | 9/2009 | Luloh et al. |
| 2010/0030108 A1 | 2/2010 | Anderson et al. |
| 2010/0145374 A1 | 6/2010 | Perkins |
| 2010/0286691 A1 | 11/2010 | Kerr et al. |
| 2010/0317998 A1 | 12/2010 | Hibner et al. |
| 2011/0054349 A1 | 3/2011 | Hibner |
| 2011/0295293 A1 | 12/2011 | Agahi |
| 2011/0295296 A1 | 12/2011 | Charles |
| 2012/0116391 A1 | 5/2012 | Houser et al. |
| 2012/0157906 A1 | 6/2012 | Underwood et al. |
| 2012/0158029 A1 | 6/2012 | Underwood et al. |
| 2013/0144317 A1 | 6/2013 | Valencia |

OTHER PUBLICATIONS

International Search Report for PCT/US2012/069216, dated Feb. 26, 2013, 2 pages.

International Preliminary Report on Patentability and Written Opinion of the International Searching Authority, International Application No. PCT/US2011/062797, dated Mar. 9, 2012, 9 pages.

Brushless DC Motor, http://www.allaboutcircuits.com/vol_2/chpt_1316.html, Dec. 18, 2010, retrieved using the "Internet Wayback Machine," 3 pages, vol. 2, Chapter 13. Last accessed Jun. 27, 2014.

Supplemental European Search Report for Application No. 11851826.5, Publication No. 2648630, Published Oct. 16, 2013, 8 pages.

International Preliminary Report on Patentability and Written Opinion of the International Searching Authority, International Application No. PCT/2012/069216, dated Jun. 24, 2014, 11 pages.

Supplemental European Search Report for Application No. EP12860860.1, Publication No. EP2793717, Published Oct. 29, 2014, 6 pages.

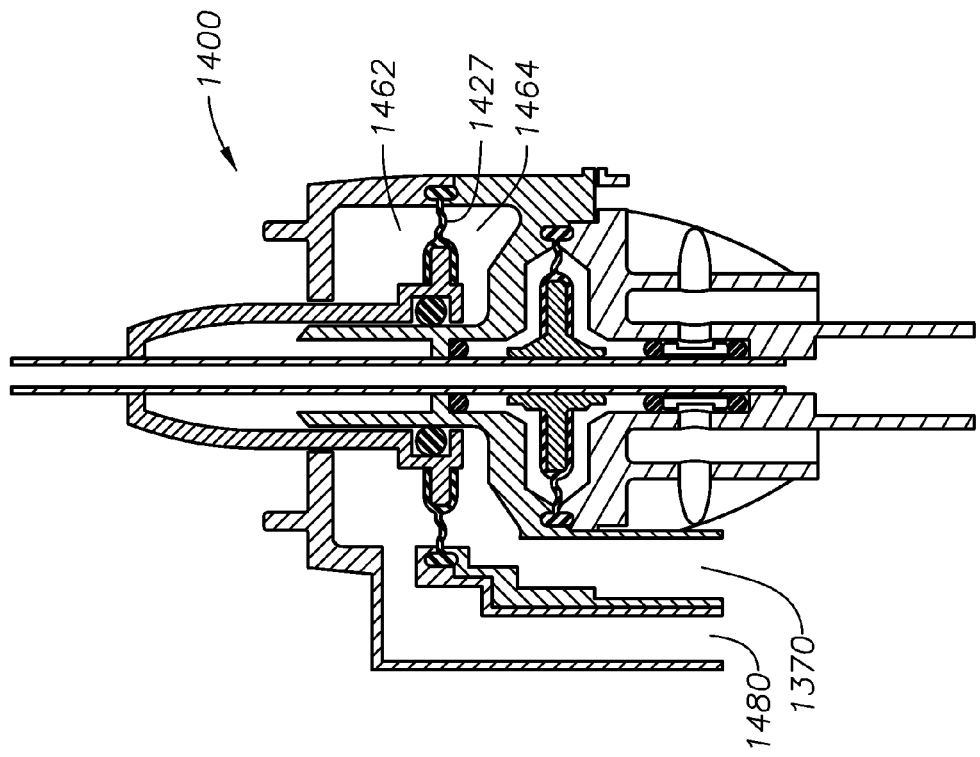
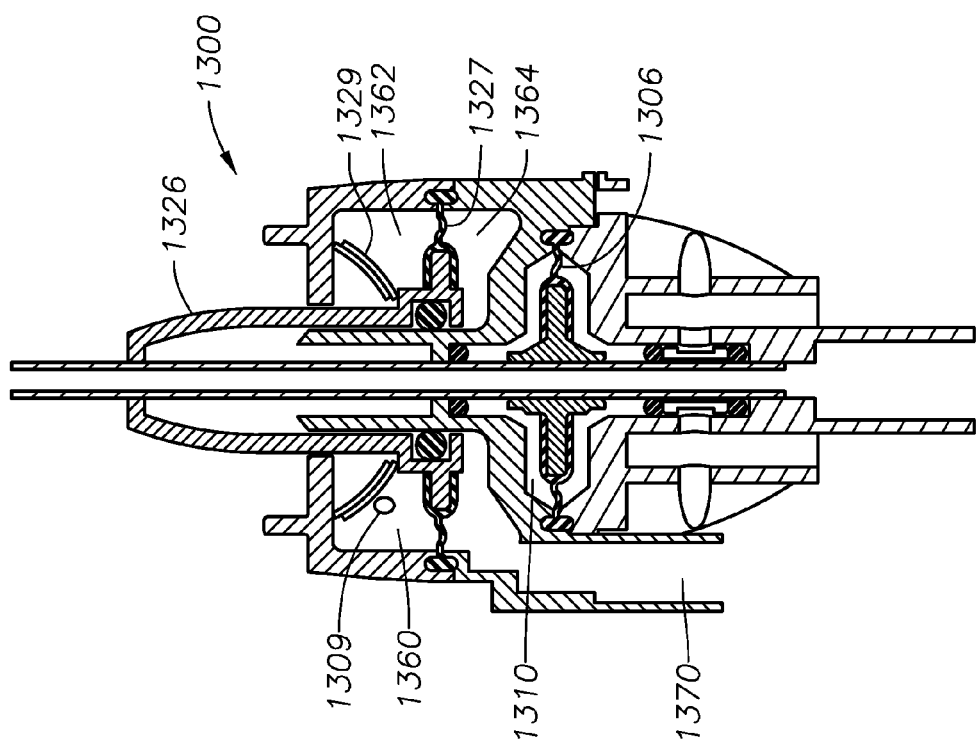
Fig. 14A
Fig. 14B

VITRECTOMY PROBE WITH ADJUSTABLE CUTTER PORT SIZE

CROSS-REFERENCE TO RELATED APPLICATIONS

This application is a divisional application of prior application Ser. No. 13/219,017, filed Aug. 26, 2011, which is a continuation of prior application Ser. No. 12/974,722, filed Dec. 21, 2010, the entire contents of both being incorporated herein by reference. This application also relates to application Ser. No. 12/974,740, filed Dec. 21, 2010; application Ser. No. 13/219,089, filed Aug. 26, 2011; application Ser. No. 13/218,923, filed Aug. 26, 2011; and application Ser. No. 13/218,826, filed Aug. 26, 2011.

TECHNICAL FIELD

The present disclosure relates to an ophthalmic microsurgical instrument. Particularly, the present disclosure is directed to a vitreoretinal surgical instrument, e.g., a vitrectomy probe, having a user-selectable cutter port size.

BACKGROUND

Vitrectomy probes are used during vitreoretinal surgery to remove ocular tissues, such as vitreous humor and membranes covering the retina. These probes have a port for drawing in and dissecting tissues. The port opens a fixed amount, tissue is drawn into the port, the port closes, severing the tissue, and the tissue is aspirated. This action may be repeated to remove desired tissues.

SUMMARY

According to one aspect, the disclosure describes a control system for operating a vitrectomy probe and controlling a port size of the vitrectomy probe. The control system may include an output valve, a first output port operable to communicate pneumatic pressure to the vitrectomy probe, a second output port operable to communicate pneumatic pressure to the vitrectomy probe, a first conduit coupled to the output valve and operable to communicate pneumatic pressure to the output valve, a venting control valve, a second conduit extending between the output valve and the venting control valve operable to conduct pneumatic pressure from the output valve to the venting control valve, a first outlet coupled to the venting control valve and open to the atmosphere, and a controller. The first output port may be coupled to the output valve, and the second output port may be coupled to the output valve. The controller may be operable to oscillate the output valve between a first position in which the first conduit is in communication with the first output port and the second conduit is in communication with the second outlet port, and a second position in which the first conduit is in communication with the second output port and the first output port is in communication with the second conduit, the output valve maintained at the first position and the second position for a selected time period; move the venting control valve from a first position in which the second conduit communicates at a first amount with the second outlet and a second position in which the second conduit communicates a second amount with the second outlet when the output valve is in one of the first position or second position; maintain the venting control valve in the second position for a first period of time less than the selected period of time when the output valve is in one of the first position or second position to define the port size of the vitrectomy probe; and move the exhaust control valve from the first position to the second position after the first period of time has elapsed.

Another aspect is directed to a system for performing a vitrectomy. The system may include a vitrectomy probe and a control system. The vitrectomy probe may include a first inlet port operable to conduct pneumatic pressure to an oscillator, a second inlet port operable to conduct pneumatic pressure to the oscillator, and a cutter. The cutter may include a first portion and a second portion. The oscillator may be operable to reciprocate the first portion relative to the second portion, and an amount of movement of the first portion relative to the second portion defines a port size of the cutter. The oscillator may be operable to reciprocate at least a portion of the cutter. The control system may include an output valve, a first output port operable to provide communication between the first inlet port of the vitrectomy probe and the output valve, a second output port operable to provide communication between the second inlet port of the vitrectomy probe and the output valve, a first conduit coupled to the output valve and operable to provide communication with the output valve, a venting control valve, a second conduit extending between the output valve and the venting control valve operable to conduct pneumatic pressure from the output valve to the venting control valve, a first outlet coupled to the venting control valve and open to the atmosphere, and a controller.

The venting control valve may be operable to selectively vent pneumatic pressure from the second conduit to the atmosphere. The controller may be operable to oscillate the output valve between a first position in which pneumatic pressure is communicated from the first conduit to the first output port and pneumatic pressure is communicated from the second output port to the second conduit, and a second position in which pneumatic pressure is communicated from the first conduit to the second output port and pneumatic pressure is communicated from the first output port to the second conduit, the output valve maintained at the first position and the second position for a selected time period; and move the venting control valve between a first position in which a first amount of pneumatic pressure from the second conduit is vented to the atmosphere through the first outlet and a second position in which a second amount of pneumatic pressure is vented to the atmosphere through the first outlet. The controller may be operable to maintain the exhaust control valve at the first position for a first period of time less than the selected period of time when the output valve is in the second position and move the exhaust control valve from the first position to the second position after the first period of time has elapsed to define the port size of the vitrectomy probe.

The various aspects may include one or more of the following features. The first amount of communication may be greater than the second amount of communication. The venting control valve may be an on/off valve, and the first amount of communication between the second conduit and the second outlet when the venting control valve is in the first position may be a full amount of communication between the second conduit and the second outlet. The second amount of communication between the second conduit and the second outlet when the venting control valve is in the second position may be no communication between the second conduit and the second outlet.

The venting control valve may be a proportional valve, and the first amount of communication may be greater than the second amount of communication. The venting control valve may be a proportional valve. The first amount of communication provided between the second conduit and the second outlet when the venting control valve is in the first position may be a first variable amount of communication, and the second amount of communication provided between the second conduit and the second outlet when the venting control valve is in the second position may be a second variable amount of communication between the second conduit and the second outlet. The first variable amount may be different than the second variable amount. An isolation valve may also be included, and the first conduit may extend between the isolation valve and the output valve. An inlet conduit may be coupled to the isolation valve and may be operable to communicate pneumatic pressure to the isolation valve. A second outlet may be coupled to the isolation valve and may be open to the atmosphere. The controller may also be operable to move the isolation valve between a first position in which the inlet conduit is in communication with the second outlet to vent pneumatic pressure in the first outlet conduit to the atmosphere and a second position in which the inlet conduit is in communication with the first conduit to conduct pneumatic pressure to the output valve.

A first pressure sensor and a second pressure sensor may also be included. The first pressure sensor may be coupled to the first output port, and a second pressure sensor coupled to the second output port. The controller may also be operable to receive a first signal from the first pressure sensor corresponding to pneumatic pressure at the first output port and a second signal from the second pressure sensor corresponding to pneumatic pressure at the second output port. The controller may also be operable to move the isolation valve to the first position if the first pressure signal or the second pressure signal is outside of a selected range.

The various aspects may also include one or more of the following features. The first amount of pneumatic pressure may be greater than the second amount of pneumatic pressure. The venting control valve may be an on/off valve. The first position of the venting control valve may be a fully open position, and the second position of the venting control valve may be a fully closed position. The venting control valve may be a proportional valve. The first amount of pneumatic pressure vented to the atmosphere may be a first variable amount of communication, and the second amount of communication between the second conduit and the second outlet when the venting control valve is in the second position may be a second variable amount of communication between the second conduit and the second outlet. The first variable amount of communication may be different than the second variable amount of communication. The first variable amount of communication may be greater than the second variable amount of communication.

The various aspects may also include one or more of the following features. The system may also include an isolation valve, an inlet conduit coupled to the isolation valve and operable to communicate pneumatic pressure to the isolation valve, and a second outlet coupled to the isolation valve and open to the atmosphere. The first conduit may extend between the isolation valve and the output valve. The controller may be operable to move the isolation valve between a first position in which the inlet conduit is in communication with the second outlet to vent pneumatic pressure in the first outlet conduit to the atmosphere and a second position in which the inlet conduit is in communication with the first conduit to conduct pneumatic pressure to the output valve. The system may also include a first pressure sensor coupled to the first output port and a second pressure sensor coupled to the second output port. The controller may be operable to receive a first signal from the first pressure sensor corresponding to pneumatic pressure at the first output port and a second signal from the second pressure sensor corresponding to pneumatic pressure at the second output port and move the isolation valve to the first position if the first pressure signal or the second pressure signal is outside of a selected range.

The details of one or more implementations of the present disclosure are set forth in the accompanying drawings and the description below. Other features, objects, and advantages will be apparent from the description and drawings, and from the claims.

DESCRIPTION OF DRAWINGS

FIG. 14A is another cross-sectional view of the vitrectomy probe of FIG. 13 showing a detail of an example stroke limiter.

FIG. 14B show a cross-sectional view of a detail of another example stroke limiter.

DETAILED DISCLOSURE

The present disclose describes microsurgical instruments including a variable-sized port for removing tissues. Particularly, the present disclosure describes ophthalmic vitrectomy probes with a user-selectable, variable-sized port used, for example, in posterior segment ophthalmic surgeries. A medical practitioner, such as a surgeon, can control the probe's port size to maximize cutting efficiency and tissue flowability. Alteration of the port size may be accomplished in numerous ways. For example, the port size may be adjusted pneumatically, mechanically, electrically, manually, or by a combination of any of these. Some implementations may utilize a mechanical stop to control a size of the port opening. In other implementations, a size of the port opening may be controlled pneumatically. While the examples set out below are made with respect to ophthalmic surgical procedures, the disclosure is not so limited. Rather, the examples provided are merely that, and the scope of the disclosure may be applicable to any surgical instrument for which a variable sized port may be desirable or to which a variable-sized port may be adapted.

Figure 1:
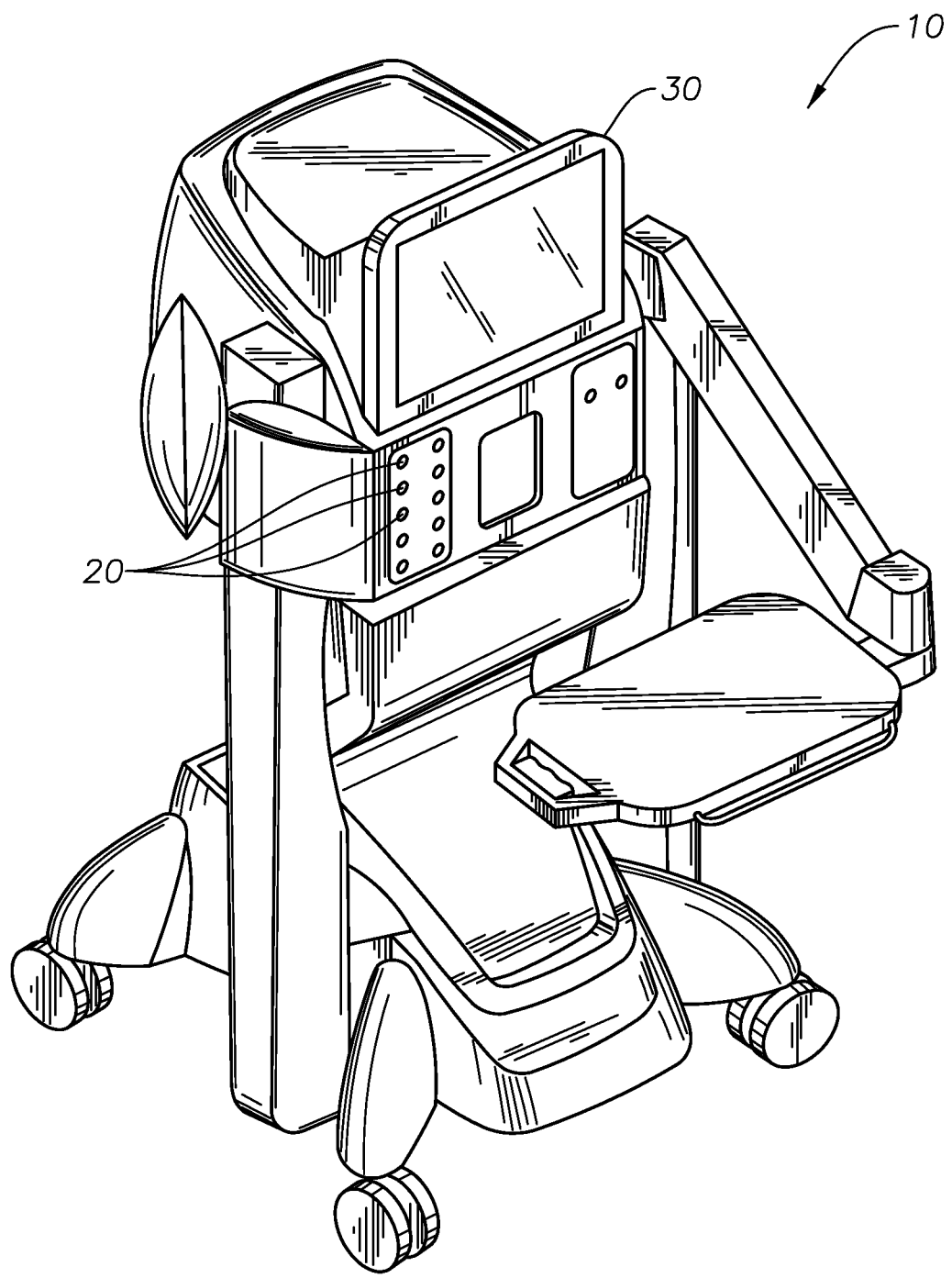
FIG. 1 shows an example surgical console.

FIG. 1 shows an example surgical console (interchangeably referred to as "console") 10 within the scope of the present disclosure. The surgical console may be a vitreoretinal surgical console, such as the Constellation® surgical console produced by Alcon Laboratories, Inc., 6201 South Freeway, Fort Worth, Tex. 76134 U.S.A. The console 10 may include one or more ports 20. One or more of the ports 20 may be utilized for providing infusion and/or irrigation fluids to the eye or for aspirating materials from the eye. The console 10 may also include a display 30 for interfacing with the console 10, such as to establish or change one or more operations of the console 10. In some instances, the display 30 may include a touch-sensitive screen for interacting with the console 10 by touching the screen of the display 30. A probe, such as a vitrectomy probe may be coupled to a port 20 for dissecting ocular tissues and aspirating the ocular tissues from the eye.

Figure 2:
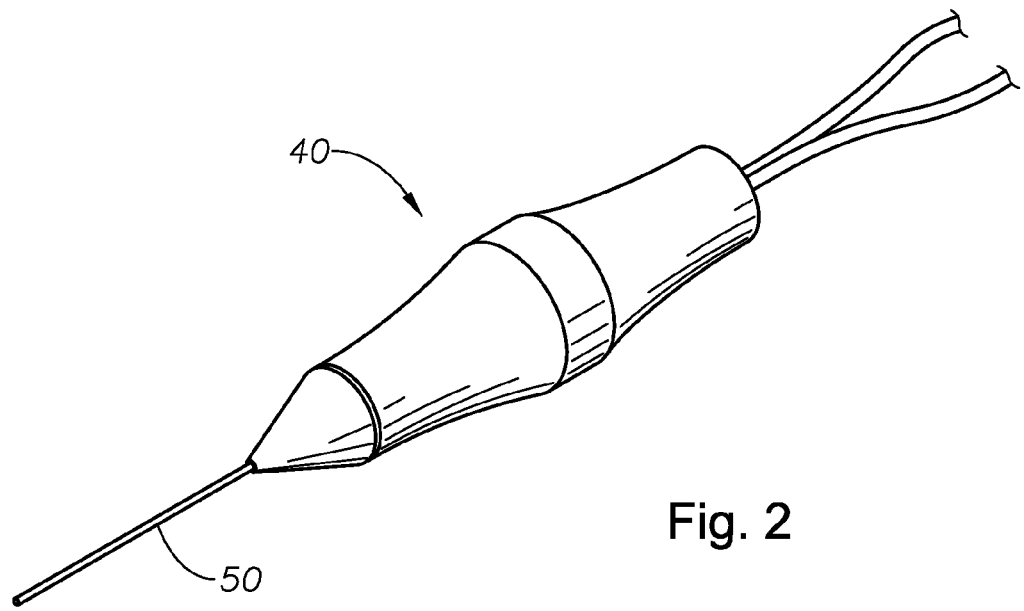
FIG. 2 shows an example vitrectomy probe having a cutter with an adjustable-sized cutting port.
Figure 3:
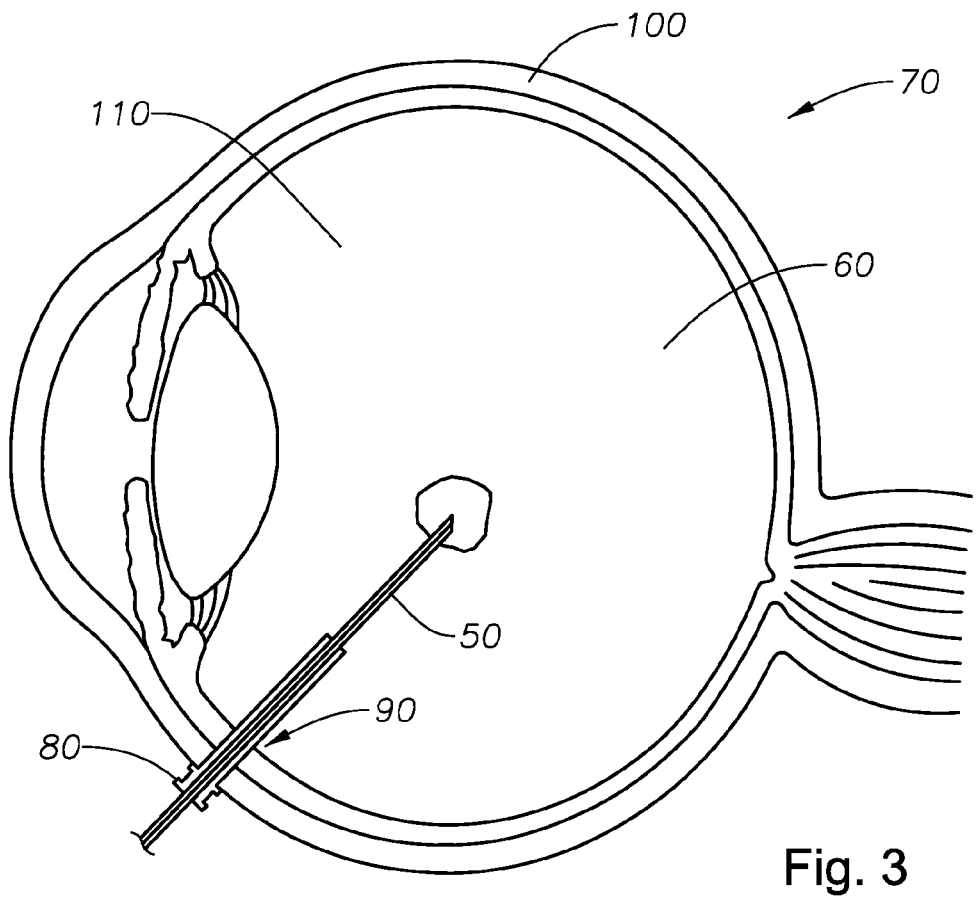
FIG. 3 shows a cross-sectional view of an eye in which a cutter of a vitrectomy probe extends into a posterior segment of the eye.

FIG. 2 shows an example vitrectomy probe 40. The probe 40 includes a cutter 50. As illustrated in FIG. 3, during an ophthalmic surgical procedure, such as a retinal surgical procedure, the cutter 50 may be inserted into the posterior segment 60 of the eye 70, such as through a cannula 80 disposed in an incision 90 through the sclera 100 of the eye 70, to remove and aspirate ocular tissues. For example, during a retinal surgical procedure, the cutter 50 may be inserted into the posterior chamber 60 of the eye 70 to remove vitreous humor (interchangeably referred to as "vitreous") 110, a jelly-like substance that occupies the volume defined by the posterior segment 60. The cutter 50 may also be used to remove membranes covering the retina or other tissues.

FIGS. 4-8 show detailed, cross-sectional views of an example cutter 50 with ports 120 adjusted to various sizes. The example cutter 50 may include a hollow outer cutting member 130. The outer cutting member 130 in which an opening 115 is formed. The cutter 50 may also include a hollow inner cutting member 140 coaxially arranged within the outer cutting member 130 and slideable therein. The inner cutting member 140 may also include a cutting edge 150. The cutting edge 150 and the opening 115 may define the port 120. Thus, for example, a position of the cutting edge 150 relative to the opening 115 may define the size of the port 120. In operation, tissue may enter into the cutter 50 through the port 120 and be dissected by the cutting edge 150 as the inner cutting member 140 is reciprocated within the outer cutting member 130. The tissue may be dissected by the cutting edge 150 as the inner cutting member 140 extends within the outer cutting member 130, closing the port 120 (see, e.g., FIG. 8). A vacuum may also be generated within an interior channel 160 of the cutter 50 to aspirate the dissected tissue.

In some implementations, the inner cutting member 140 is reciprocated within the outer cutting member 130 pneumatically. However, the disclosure is not so limited. Rather, the cutter 50 may be operated in other ways. For example, the cutter 50 may be operated electrically, hydraulically, or in any number of other ways. Therefore, the description of utilizing pneumatics to operate the cutter 50 in one or more of the implementations is provided merely as an example and is not intended to be limiting.

Figure 4:
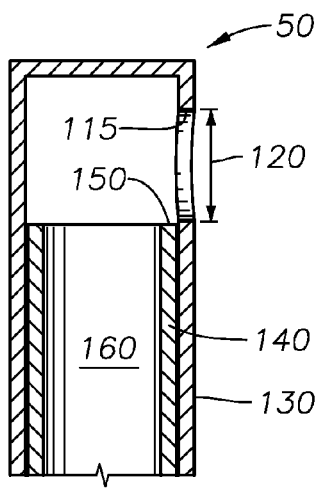
FIGS. 4-8 are detailed cross-sectional views of a vitrectomy cutter showing cutter ports with different sizes.
Figure 5:
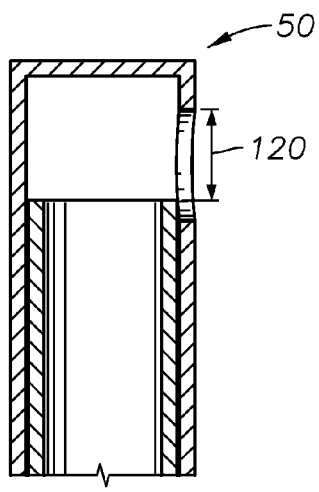
Figure 6:
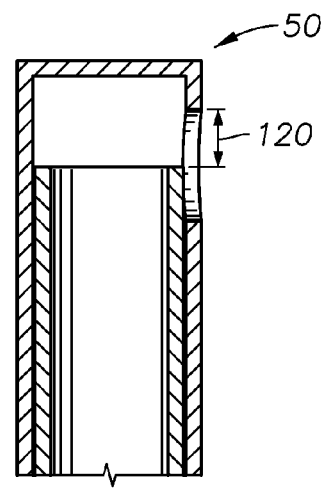
Figure 7:
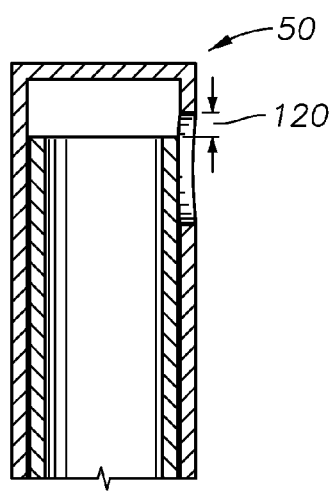
Figure 8:
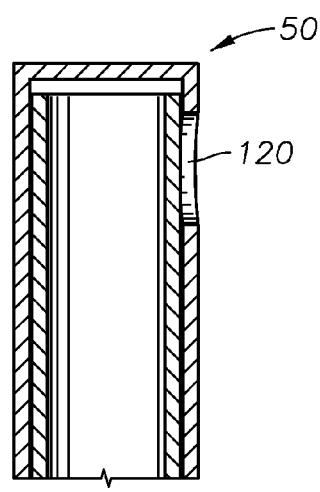

During an ophthalmic surgical procedure, it may be desirable to change a size of the port 120. For example, a port size may be changed to maximize cutting efficiency and tissue flowability. Further, a cutter having an adjustable port size provides for altering, for example, a duty cycle, cut rate, and port opening independent of each other. FIGS. 4-8 illustrate a cutter 50 having port 120 adjusted to different sizes. For example, FIG. 4 shows the size of port 120 adjusted to 100 percent; FIG. 5 shows the size of port 120 at approximately 75 percent; FIG. 6 shows the size of port 120 at approximately 50 percent; and FIG. 7 shows the size of port 120 at approximately 25 percent. FIG. 8 shows the port 120 in a closed configuration. While FIGS. 4-8 show port sizes at 75%, 50%, 25%, and closed are described, these port sizes are not intended to be limiting. Rather, it is within the scope of the disclosure that the port size of a probe may be adjusted to any desired size.

Figure 9:
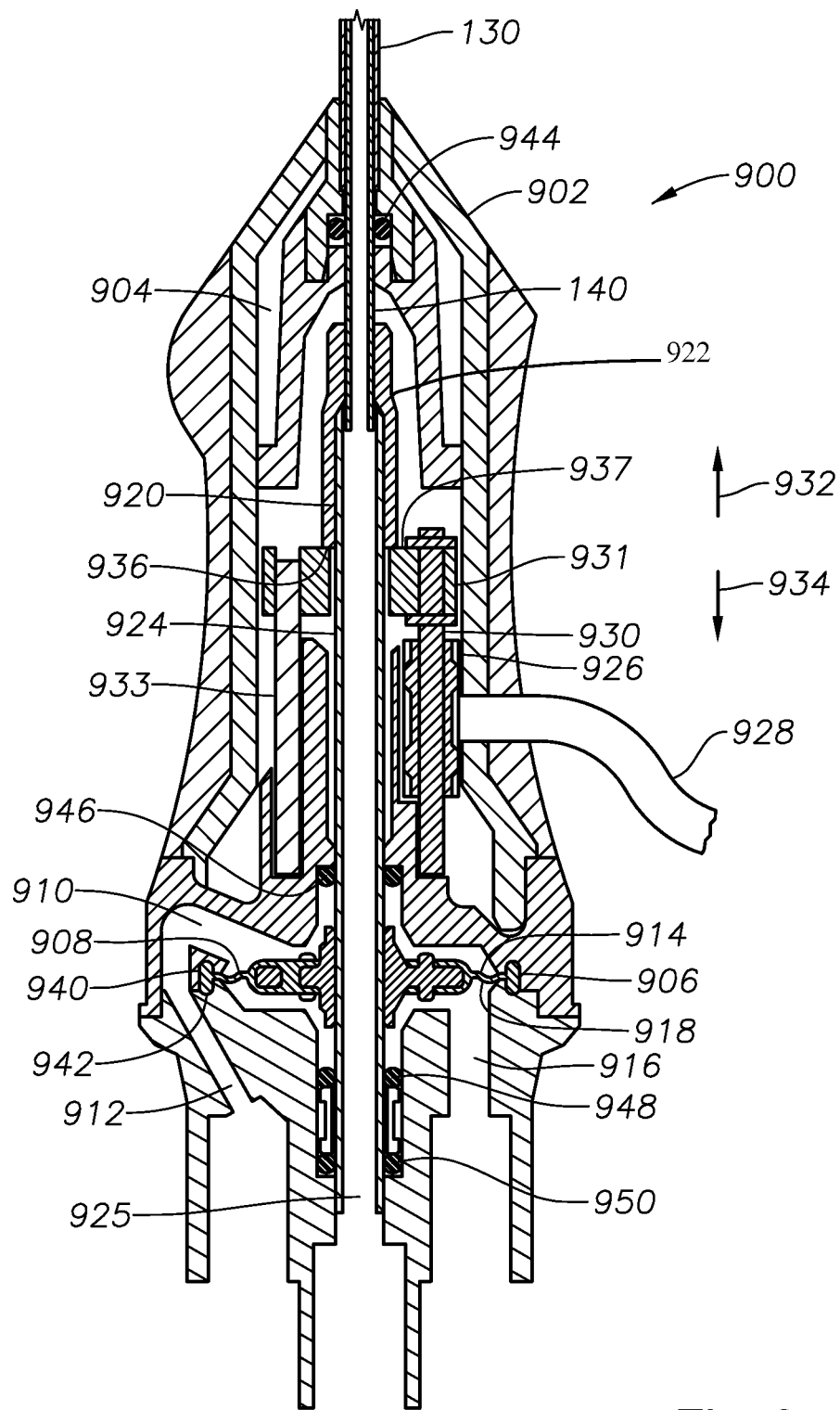
FIG. 9 shows a cross-sectional view of an example vitrectomy probe having a user-controllable cutter port size adjustable with a piezoelectric motor.

In some implementations, the probe may include a piezoelectric linear motor to alter the port size. FIG. 9 shows a partial cross-sectional view of an example probe 900. The probe 900 may include a housing 902 defining an interior chamber 904, and an oscillator or motor 906. The outer cutting member 130 may be fixedly coupled to the housing 902. The motor 906 may include a diaphragm 908 disposed in a pneumatic chamber 910. A periphery 940 of the diaphragm 908 may be retained in a groove 942 formed in the probe 900. The pneumatic chamber 910 may include a first passage 912 for communicating a pneumatic pressure to a first surface 914 of the diaphragm 908 and a second passage 916 for communicating a pneumatic pressure to a second surface 918 of the diaphragm 908. Alternating pneumatic pressure between the first passage 912 and the second passage 916 displaces the diaphragm 908 in opposing directions, causing the diaphragm 908 to oscillate.

The inner cutting member 150 is coupled to the diaphragm 908. Consequently, the inner cutting member 140 is made to oscillate within the probe 900 relative to the outer cutting member 130. The inner cutting member 140 may be coupled to the diaphragm 106 by a tube 920 and a hollow coupling 922. The inner cutting member 140, the hollow coupling 922, and the tube 920 form an interior assembly 924 and define a passage 925 that may be utilized for aspirating fluid, tissue, and other material from the eye.

The probe 900 may also include seals 944, 946, 948, and 950. Other implementations may include additional, fewer, or different seals than those described. The seals 944-950 may be adapted to prevent and/or substantially reduce passage of fluid thereby. In some implementations, the seals 944-950 may also provide low resistance to movement of the interior assembly 924.

The probe 900 may also include a piezoelectric linear motor (interchangeably referred to as "piezoelectric motor") 926. In some implementations, the piezoelectric motor 926 may be an ultrasonic linear actuator. The piezoelectric motor 926 may be fixedly secured within the housing 902. For example, the piezoelectric motor 926 may be secured within the housing 902 with a fastener, adhesive, interference fit, retaining clip, or in any other desired manner. In some instances, the piezoelectric motor 926 may be received into a receptacle formed in the housing. Power may be provided to the piezoelectric motor 926 via a cable 928 extending through the housing 902. In some instances, the piezoelectric motor 926 may be an SQL-1.8-6 SQUIGGLE® Piezo Linear Motor produced by New Scale Technologies, Inc., of 121 Victor Heights Parkway, Victor, N.Y. 14564. However, other types of piezoelectric motors may be used and are within the scope of the disclosure.

The piezoelectric motor 926 may include a lead screw 930. Application of an AC drive voltage signal pair at a first phase offset causes lead screw 930 to move in the direction indicated by arrow 932. Application of an AC drive voltage signal pair at second phase offset different than the first phase offset causes lead screw 930 to move in an opposite direction, corresponding to arrow 934. A moveable member 931 may be coupled to the lead screw 930 and be moveable therewith. Further, a guide 933 coupled to the housing 902 may be included to align the moveable member 931 as the moveable member 931 is moved within the housing 902. That is, the moveable member 931 may be guided during movement by the guide 933. For example, the guide 933 may prevent the member 931 from being becoming misaligned and binding within the probe 900.

During operation, a surface 937 of the moveable member 931 may engage a lower surface 936 of the coupling 922 to define a fully retracted position of the inner cutting member 140. As a position of the lead screw 930 is changed, the position of the moveable member 931 is changed, and the location at which the moveable member 931 engages the coupling 922 changes. Consequently, by adjusting a position of the lead screw 930, the amount of movement of the inner cutting member 140 in the direction of arrow 934 may be altered, thereby changing the size of the port 120. It is noted that movement of the inner cutting member 140 in the direction of arrow 934 corresponds to an opening of the port 120 shown, for example, in FIGS. 4-8.

While the moveable member 931 is described as engaging the coupling 922, the moveable member 931 may be adapted to engage other parts of the probe 900. For example, the moveable member 931 may be adapted to engage another portion of the interior assembly 924 to limit the movement of the inner cutting member 140. Still further, in some implementations, the piezoelectric motor 926 may be coupled to the interior assembly 924 and the lead screw 930, via the moveable member 931, may engage a portion of the housing 902 to limit a stroke of the inner cutting member 140.

In some instances, though, the moveable member 931 and the guide 933 may be omitted. In such implementations, the lead screw 930 may directly engage a portion of the interior assembly 924, such as the coupling 922 to limit a stroke of the inner cutting member 140. While the probe 900 is described above as including a piezoelectric motor 926, any suitable rotational drive motor may be used. For example, in some implementations, a vitrectomy probe may include a stepper motor or, in other implementations, a DC motor acting against a torsional spring to adjust the port size. These are provided merely as examples. Thus other rotational drive devices may be utilized to adjust the port size.

Figure 10:
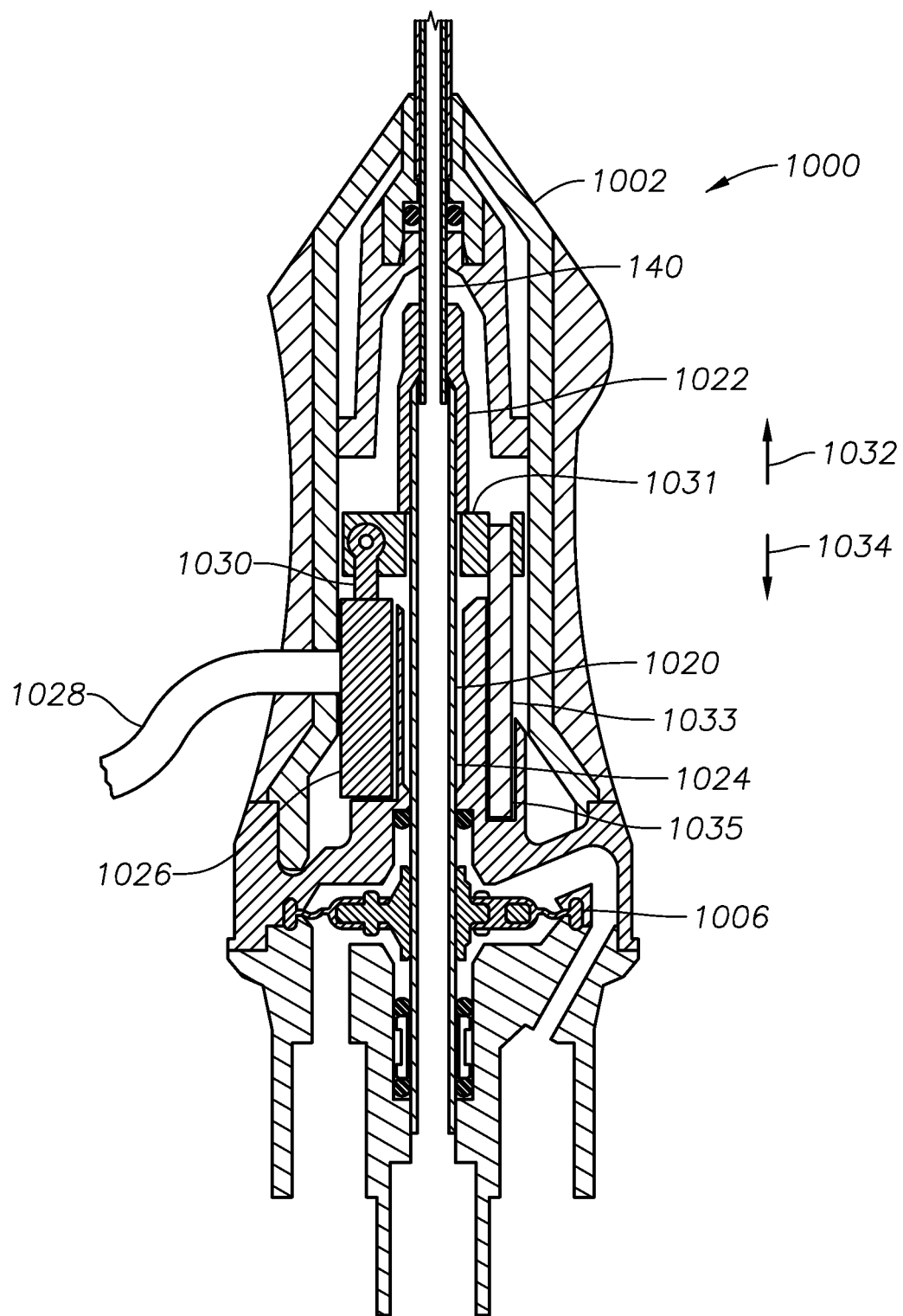
FIG. 10 shows a cross-sectional view of an example vitrectomy probe including a shape memory alloy element for altering a size of the cutting port of the probe.

FIG. 10 shows another example probe having an adjustable sized port according to another implementation. In the example shown in FIG. 10, the construction of probe 1000 may be substantially the same as the construction of probe 900 discussed above. However, the construction of probes 900 and 1000, as well as the other probes described herein, are provided merely as examples, and are not intended to be limiting. Thus, probes having constructions other than those examples provided herein are within the scope of the disclosure.

The probe 1000 may include a housing 1002, an oscillator or motor 1006 (which may be similar to the motor 906, described above), and an SMA ("shape memory alloy") element 1026 rather than a piezoelectric linear motor. In some instances, the SMA element 1026 may be a NanoMuscle DS-CE linear actuator produced by MIGA Motor Company of 1241 Adams Street #1147, Saint Helena, Calif. 94574. However, this example SMA element is provided merely as an example. Thus, other types of SMA elements may be used and are, hence, within the scope of the disclosure.

In some implementations, the SMA element 1026 may be coupled to the housing 1002. For example, the SMA element 1026 may be coupled to the housing 1002 by being received and retained into a receptacle formed in the housing 1002. In some instances, the SMA element 1026 may be coupled to the housing, such as with a fastener, an adhesive, a retaining clip, or in any other desired manner.

The SMA element 1026 may include a shaft 1030. In some implementations, the shaft 1030 may be coupled to a moveable member 1031. In some instances, the probe 1000 may also include a guide 1033. The guide 1033 may be coupled to probe 1000, such as to the housing 1002. For example, as illustrated in FIG. 10, the guide rod 1033 may be disposed in a slot 1035. A position of the shaft 1030 may be altered by application of electrical power to the SMA element 1026, such as via cable 1028. The power cable 1128 may be coupled to the console 10, and the console 10 may be operable to adjust the electrical power applied to the SMA element based, for example, on an input to the console 10 by a user. Input from a user to the console 10 may be provided via an input device, such as a touch screen, button, slider, footswitch, or other input device. The implementation of user input described above may be utilized in the cases of the other example probes described herein.

Application of electrical power to the SMA element 1026 may cause the shaft 1030 and member 1031 to move in the direction of arrow 1032. The member 1031 may be guided during movement by the guide 1033. For example, the guide 1033 may prevent the member 1031 from being becoming misaligned and binding within the probe 1000. The member 1031 may engage the coupling 1022, thereby limiting the stroke of inner cutting member 140 in the direction of arrow 1034 and defining a fully retracted position of the inner cutting member 140. As more power is applied to the SMA element 1026, the shaft 1030 and, correspondingly, the member 1031 may extend a greater distance in the direction of arrow 1032. Reduction or elimination of the amount of power applied to the SMA element 1026 may cause the shaft 1030 and member 1031 to retract and move in the direction of arrow 1034. Consequently, an extent to which the shaft 1030 may be extended or retracted may be controlled by an amount of power applied to the SMA element 1026 and, hence, a location at which the member 1031 and the coupling 1022 contact each other. Thus, the SMA element 1026 may be utilized as a stroke limiter for the probe 1000.

In some instances, though, the moveable member 1031 and the guide 1033 may be omitted. In such implementations, the shaft 1030 may directly engage a portion of the interior assembly 1024, such as the coupling 1022 to limit a stroke of the inner cutting member 140.

While the above examples are explained with the shaft 1004 engaging the coupling 1022, the shaft 1030 and/or moveable member 1031 may be made to engage another portion of the probe 1000 to limit the stroke of the inner cutting member 140.

For example, the shaft 1030 and/or moveable member 1031 may be made to engage another portion of interior assembly 1024, which may include the inner cutting member 140, the hollow coupling 1022, and tube 1020. In still other implementations, the SMA 1026 may be coupled to the interior assembly 1024, and the shaft 1030 may be adapted to engage, directly or indirectly, a portion of the probe 1000 that is stationary relative to the interior assembly 1024. For example, the shaft 1030 may be adapted to engage a portion of the housing 1002.

Figures 11A, 11B:
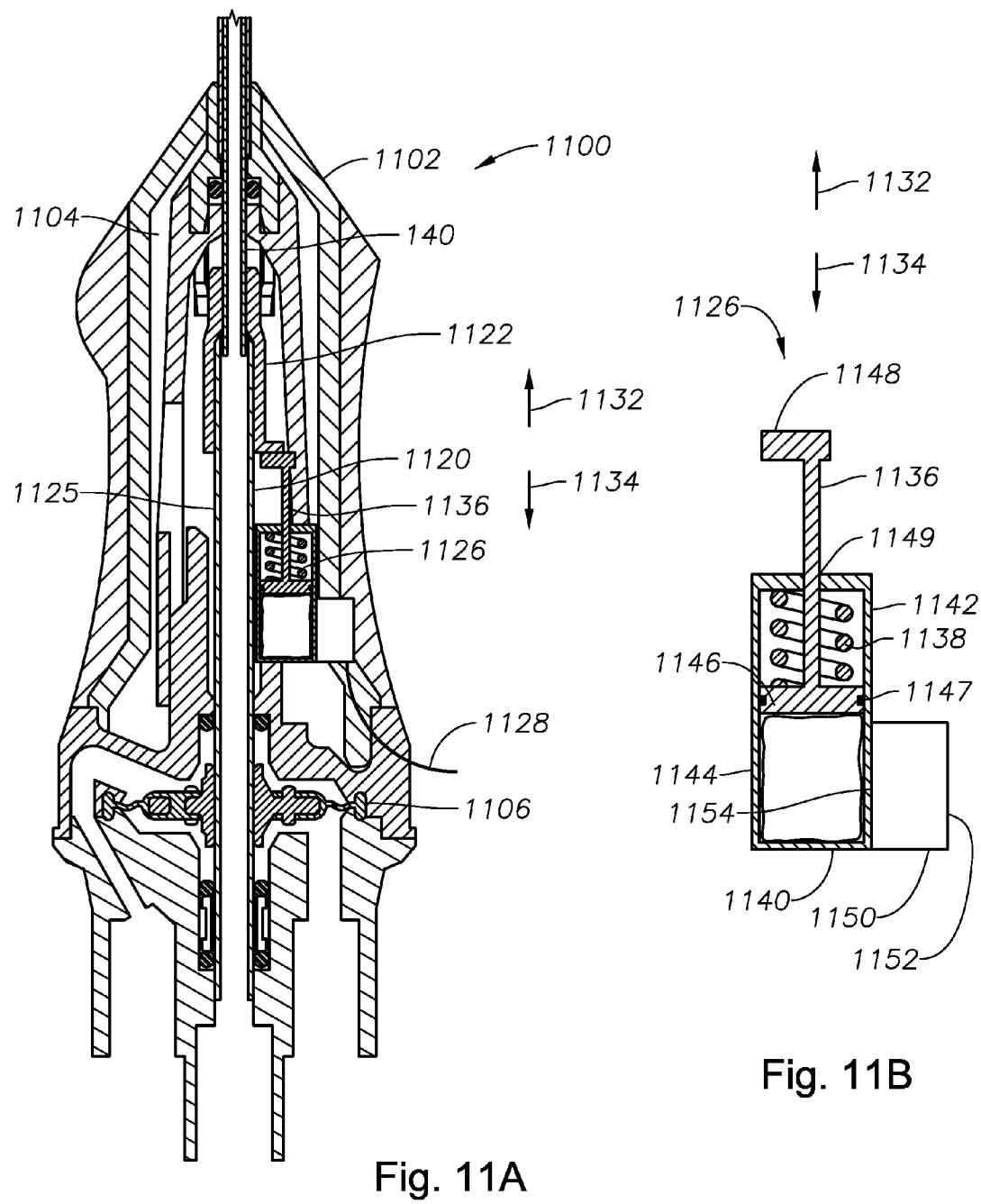
FIG. 11A shows a cross-sectional view of an example vitrectomy probe including a temperature control device and a fluid-filled enclosure for altering a size of the cutting port of the probe.
FIG. 11B shows an example stroke limiter of the probe in FIG. 11A for adjusting the cutting port size.

FIG. 11A shows a further example probe in which the port size may be adjusted with a fluid-filled cylinder. Example probe 1100 may be similar to the probes 900 and/or 1000, described above in some respects while different in others. Probe 1100 may include a housing 1102 defining an interior chamber 1104 and a motor 1106. The probe 1100 may also include a hollow coupling 1122 and a tube 1120 coupled together with the inner cutting member 140 to form an interior assembly 1125. The interior assembly 1125 may be coupled to the motor 1106. The probe 1100 may also include a stroke limiter 1126 operable to limit the stroke of the inner cutting member 140 in the direction of arrow 1134, thereby adjusting the size of the port 120 (for example, as shown in FIGS. 4-8).

As shown in FIG. 11B, the stroke limiter 1126 may include a push rod 1136, a spring 1138, and an enclosure 1140. In some implementations, the enclosure 1140 may be fixed relative to the housing 1102. The push rod 1136 may be moveable relative to the enclosure 1140. Further, in some implementations, the spring 1138 may be omitted.

The enclosure 1140 may include a first portion 1142 housing the spring 1138 and a second, fluid-filled portion 1144. In some instances, the fluid-filled portion 1144 may contain a liquid and, in some instances, may be sealed fluid-tight. The push rod 1136 may include a piston 1146 and a protrusion 1148. A seal 1147 may be disposed between piston 1146 and a wall of the enclosure 1140, for example, to contain fluid in the second portion 1144. The protrusion 1148 of the push rod 1136 may contact the coupling 1122 during opening of the port 120 when the inner cutting member 140 moves in the direction of arrow 1134. Consequently, the protrusion 1148 provides a stop, limiting the stroke of the inner cutting member 140 during operation of the cutter 50, thereby defining a fully retraced position of cutter 140. The push rod 1136 may extend through an opening 1149 formed in the enclosure 1140. The first portion 1142 and the second portion 1144 may be separated by the piston 1146.

The stroke limiter 1126 may also include a temperature control device 1150 operable to change a temperature of a fluid contained within the second portion 1144. In some instances, the temperature control device 1150 may be a peltier cooler. According to some implementations, the peltier cooler may be a Pure Precision model 9500/007/018M produced by FerroTec of 33 Constitution Drive, Bedford, N.H. 03110. However, other types of peltier coolers may be used. Still further, the disclosure is not limited to peltier coolers. Rather, any device that produces a temperature differential may be used.

An electrical voltage may be applied to the peltier cooler to generate a temperature difference between a first side 1152 and a second side 1154 and, thereby, cause a change in the temperature of the fluid within the second portion 1144. The change in temperature of the fluid within the second portion 1144 is utilized to change a position of the push rod 1136.

Movement of the push rod 1136 in a direction indicated by arrow 1132 may be accomplished, for example, by applying a voltage to the peltier cooler to heat the fluid contained in the second portion 1144. The expanding fluid applies pressure to the piston 1146 and, therefore, a force on the piston 1146 urging the push rod 1136 to move in a direction of arrow 1132. In implementations including the spring 1138, the spring 1138 may apply an opposing force in the direction of arrow 1134. The push rod 1136 will move in the direction of arrow 1132 when the force exerted on the push rod 1136 by the fluid exceeds the biasing force of the spring 1138. In implementations containing no spring 1138, the push rod 1136 moves without influence of a spring force.

Power may be supplied to the stroke limiter 1126 via a power cable 1125. The power cable 1128 may be coupled to a surgical console, such as console 10, and the console may be operable to adjust the voltage applied to the stroke limiter based, for example, on an input to the console by a user. Input from a user to the console may be provided via an input device, such as a touch screen, button, slider, footswitch, or other input device.

The push rod 1136 may be moved in the direction of arrow 1134 by decreasing or removing the voltage from the peltier cooler and allowing the fluid within the second portion 1144 to cool or by applying a voltage opposite the voltage to move the push rod 1136 in the direction of arrow 1134. As the fluid cools, the fluid contracts, reducing the force applied to the push rod 1136, and, therefore, causing the push rod 1136 to move in the direction of arrow 1134. Where a spring 1138 is present, the force applied by the spring 1138 urges the push rod 1136 in the direction of arrow 1134. It is noted that inclusion of a spring 1138 in the stroke limiter 1126 may provide a higher resolution on position control of the push rod 1136. That is, the spring 1138 may provide for greater positional control of the push rod 1136 and, hence, the stroke limiter 1126.

Movement of the push rod 1136 in the direction of arrow 1132 or arrow 1134 moves the protrusion 1148 accordingly, causing an increase or decrease, respectively, in the stroke of the inner cutting member 140. Consequently, the size of the cutter port may be adjusted. Further, in some instances, the rate at which the push rod 1136 moves may be controlled by a voltage applied to the peltier cooler.

While the illustrated example stroke limiter 1126 utilizes a peltier cooler, other implementations may use any suitable temperature control device to adjust a temperature of the fluid contained within second portion 1146 of the enclosure. For example, temperature control devices such as a ceramic resistor.

Figure 12:
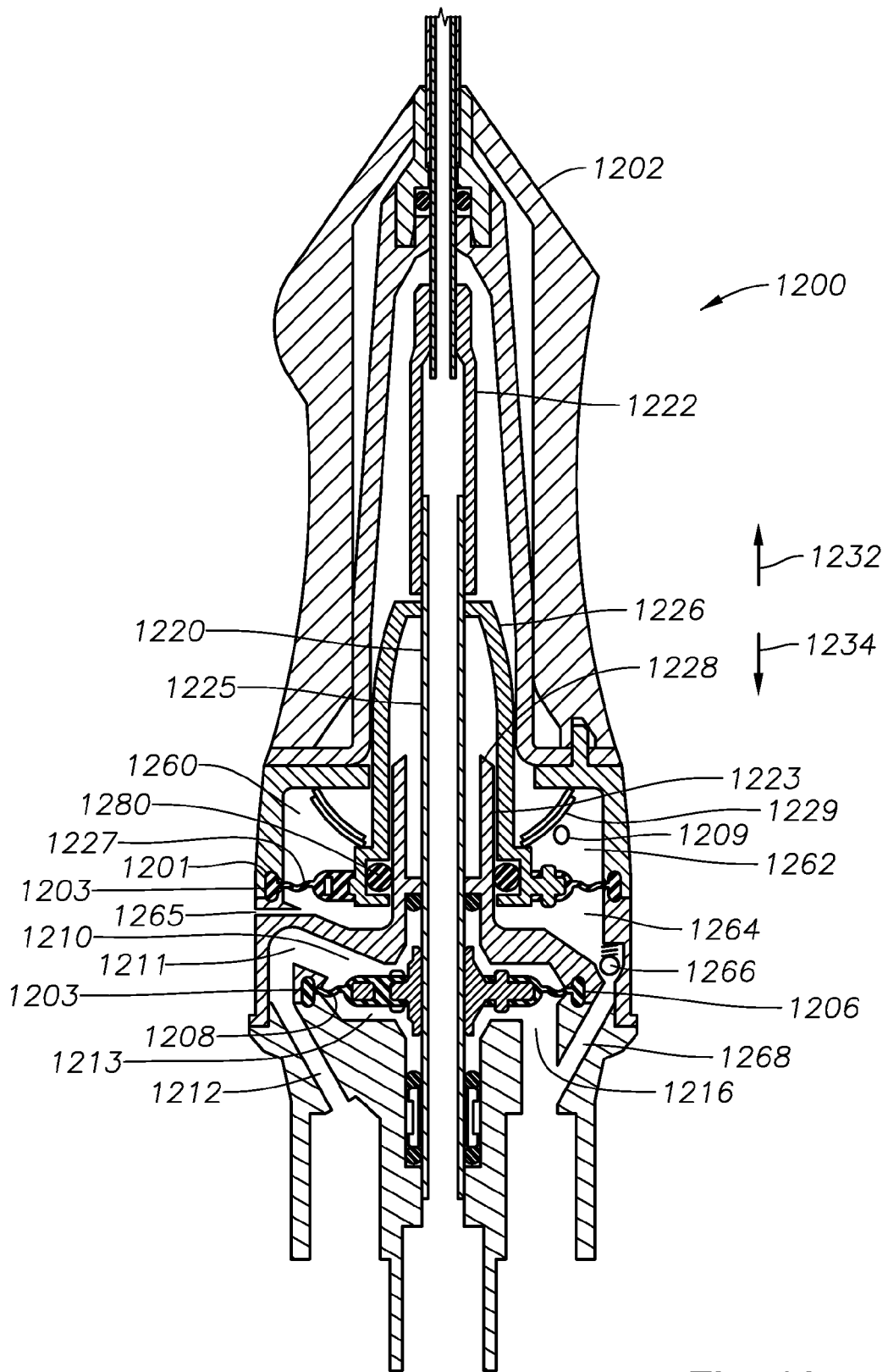
FIG. 12 shows a cross-sectional view of another example vitrectomy probe operable to adjust a size of the cutter port.

FIG. 12 shows another example probe that utilizes pressurized gas to adjust a position of a stroke limiter. As shown in FIG. 12, a probe 1200, similar to one or more of the probes described above, includes a housing 1202. The probe 1200 may also include an inner cutting member 140, a coupling 1222, and a tube 1220 forming an interior assembly 1225. The interior assembly 1225 may be coupled to a motor 1206 that may operate in a manner similar to the motor 906 described above. For example, the motor 1206 may include a diaphragm 1208 disposed in a first chamber 1210. The diaphragm 1208 bisects the first chamber 1210 into a first chamber portion 1211 and a second chamber portion 1213. A first passage 1212 communicates with the first chamber portion 1211, and a second passage 1216 communicates with the second chamber portion 1213. Pressurized gas may be alternately applied through the first passage 1212 and the second passage 1216 to oscillate the diaphragm 1208, thereby oscillating the interior assembly 1225.

The probe 1200 may also include a second chamber 1260 and a stroke limiter 1226. The stroke limiter 1226 may be longitudinally slideable on a surface 1223 of an interior sleeve 1228. In some instances, the interior sleeve 1228 may have a position fixed relative to the housing 1202. The stroke limiter 1226 may be coupled to a housing 1202 of the probe 1200 via a diaphragm 1227. A peripheral edge 1201 may be disposed in a receptacle 1203 to retain the diaphragm 1227 within the probe 1200.

The diaphragm 1227 bisects the second chamber 1260 to form a first chamber portion 1262 and a second chamber portion 1264. The diaphragm 1227 reacts to pressure differences between the first chamber portion 1262 and the second chamber portion 1264 to cause the stroke limiter 1226 to move longitudinally relative to the housing 1202 along the interior sleeve 1228. A spring 1229 may be disposed in the first chamber portion 1262 between the stroke limiter 1226 and a portion of the housing 1202 or other portion of the probe 1200 stationary relative to the stroke limiter 122. The spring 1229 provides a biasing force urging the stroke limiter 1226 in a direction of arrow 1234.

Further, the interior sleeve 1228 may form a partition between the first chamber 1210 and the second chamber 1260. A sealing member 1280 may be disposed between the stroke limiter 1226 and the sleeve 1228 to form a seal. The seal formed by the sealing member 1280 may reduce or prevent gas flow into and/or from the second chamber portion 1264. An orifice 1265 may extend between the second pneumatic chamber 1264 and an exterior of the probe 1200, providing fluid communication therebetween. An orifice 1209 may be formed between the first chamber portion 1262 and the exterior of the probe. The orifice 1209 provides for fluid flow into and out of the first chamber portion 1262 to prevent formation of a vacuum in the first chamber portion 1262 and allowing the stroke limiter 1226 to move responsive to movement of the diaphragm 1227.

A check valve 1266 may be disposed between a passage 1268 extending from the second passage 1216 and the second chamber portion 1264. The check valve 1266 may allow pressurized gas to flow into the second chamber portion 1264 from the passage 1268, but not in the opposite direction. Gas contained within the second chamber portion 1264 may be vented to the environment via the orifice 1265. In some instances, the check valve 1266 may biased so as to permit passage of a pressurized gas having a selected pressure while prohibiting passage of a pressurized gas having a pressure lower than the selected pressure.

In operation, pneumatic pressure is communicated through the passage 1268, past the check valve 1266, and into the second chamber portion 1264. For example, in some instances, the pneumatic pressure may be communicated to the second chamber portion 1264 wherein the pneumatic pressure is greater than the selected pressure. Reverse flow is prevented by the check valve 1266. Thus, the pressure of gas communicated to the second chamber portion 1264 is substantially the same as the pressure of the gas communicated to the second chamber portion 1213 of the first chamber 1210.

The pneumatic pressure acts on the diaphragm 1227, applying a force on the stroke limiter 1226 against a biasing force of the spring 1229. The stroke limiter 1226 may be displaced when the applied force on the stroke limiter 1226 exceeds the biasing force applied by the spring 1229. A spring rate of the spring 1229 may be any desired spring rate. For example, the spring rate of spring 1229 may be selected to cause the stroke limiter to displace in the direction of arrow 1232 at a desired pneumatic pressure.

Pneumatic pressure within the second chamber portion 1264 may be reduced as gas escapes through the orifice 1265. A size of the orifice 1265 may be selected that the rate at which gas escapes through the orifice 1265 from the second chamber portion 1264 is less than the rate at which pneumatic pressure is supplied to the second chamber portion 1264 as pneumatic pressure is cycled through the second passage 1216. Thus, in operation, for a given pneumatic pressure, the stoke limiter 1226 may be maintained at a desired position.

As the pneumatic pressure decreases in the second chamber portion 1264, the spring force from spring 1229 overcomes the force applied by the pneumatic pressure acting on the diaphragm 1227, causing the stroke limiter 1226 to move in the direction of arrow 1234. Therefore, the position of the stroke limiter 1226 may be adjusted to a desired position based on a pressure of the gas. Thus, for a given pneumatic pressure, the stroke limiter 1226 may displace a given amount and remain substantially at that position. A higher gas pressure may displace the stroke limiter 1226 a larger amount in the direction of arrow 1232. Similarly, a lower gas pressure may cause the stroke limiter 1226 to move in the direction of arrow 1234. Thus, the position of the stroke limiter 1226 and, consequently, the size of the cutter port, may be controlled based on the pressure of the gas.

Figure 13:
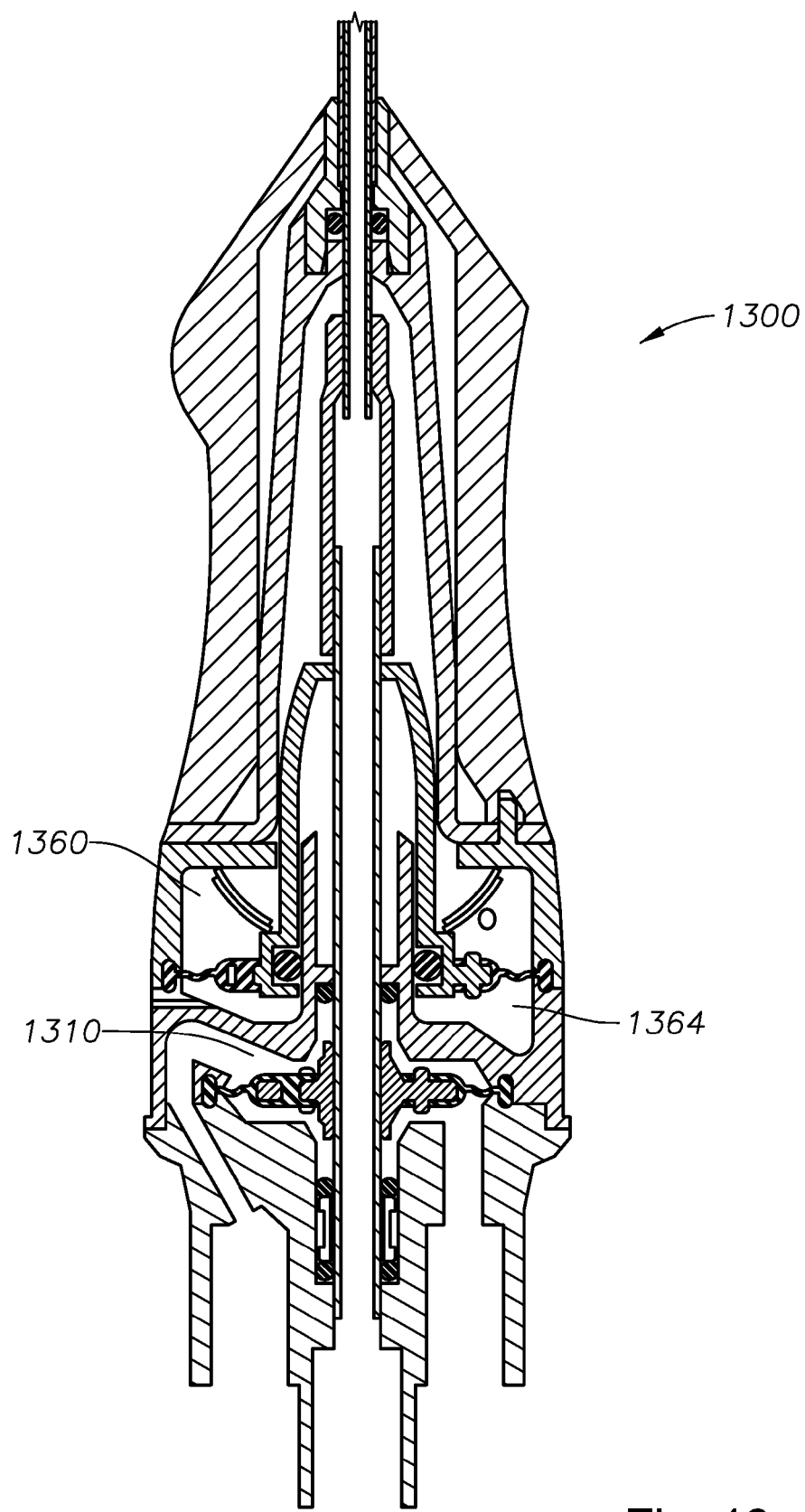
FIG. 13 shows a cross-sectional view of a further example vitrectomy probe operable to adjust a size of the cutter port.

FIGS. 13 and 14 show a further example probe 1300 and a detail thereof, respectively. The probe 1300 is similar to the probe 1200, described above. However, first chamber 1310 is pneumatically isolated from second chamber 1360.

FIG. 14A is a detail cross-sectional view of example probe 1300 taken along a different surface passing through probe 1300 than that of the cross-sectional view shown in FIG. 13. For example, the cross-section shown in FIG. 14A may be approximately 900 ° offset from the cross-sectional view shown in FIG. 13. FIG. 14A shows diaphragm 1306 disposed in the first chamber 1310 and diaphragm 1327 disposed in the second chamber 1360. Spring 1329 is also shown in first chamber portion 1362, and an orifice 1309 is formed between the first chamber portion 1362 and an exterior of the probe 1300 to provide fluid communication therebetween. A passage 1370 is in fluid communication with the second chamber portion 1364. Pneumatic pressure may be introduced into and released from the second chamber portion 1364 via a passage 1370. Thus, pneumatic pressure may be applied to the diaphragm 1327 via passage 1370 to position stroke limiter 1326 at a desired location. Further, pneumatic pressure applied to the second chamber portion 1364 to position stroke limiter 1326 may be applied independently of the pneumatic pressure utilized to operate motor 1306.

A pneumatic pressure corresponding to a desired cutter port size may be introduced into and maintained in the second chamber portion 1364 to maintain a desired position of the stroke limiter 1326. Similar to probe 1200, the spring 1329 may provide a bias force on the stroke limiter 1326. The pneumatic pressure applied to the second chamber portion 1364 may be altered when a change in position of the stroke limiter 1326 is desired. For example, the applied pneumatic pressure may be increased to reduce the cutter port size, for example, by moving stroke limiter 1326 closer to coupling 1322. Alternately, the applied pneumatic pressure may be decreased to increase the cutter port size, for example, by moving the stroke limiter 1326 away from the coupling 1322. Still further, in some instances, no pneumatic pressure may be applied to the second chamber portion 1364, providing for the port to open a maximum amount.

FIG. 14B shows a cross-section of a probe 1400 similar to the cross-section shown in FIG. 14A. However, unlike the probe 1300 shown in FIG. 14A, chamber pneumatic pressure may be supplied to first chamber portion 1462 via passage 1480 to act as a bias element. Thus, probe 1400 may not include a spring in the second chamber portion 1464. Pneumatic pressure supplied to the first chamber portion 1462 may be altered to control a size of port 120 of the probe 1400. For example, the pneumatic pressures supplied to first chamber portion 1462 via conduit 1480 and 1464 via conduit 1470 may be selected to control the port size of the cutter 1400. For example, the magnitude of the pneumatic pressure supplied to the first chamber portion 1462 may be selected to control an amount of resistance experienced by diaphragm 1327 in response to pneumatic pressure supplied to second chamber portion 1464. In still other instances, the conduit 1480 may be eliminated and a selected pressure may be introduced into and retained within the first chamber portion 1462.

Figure 15:
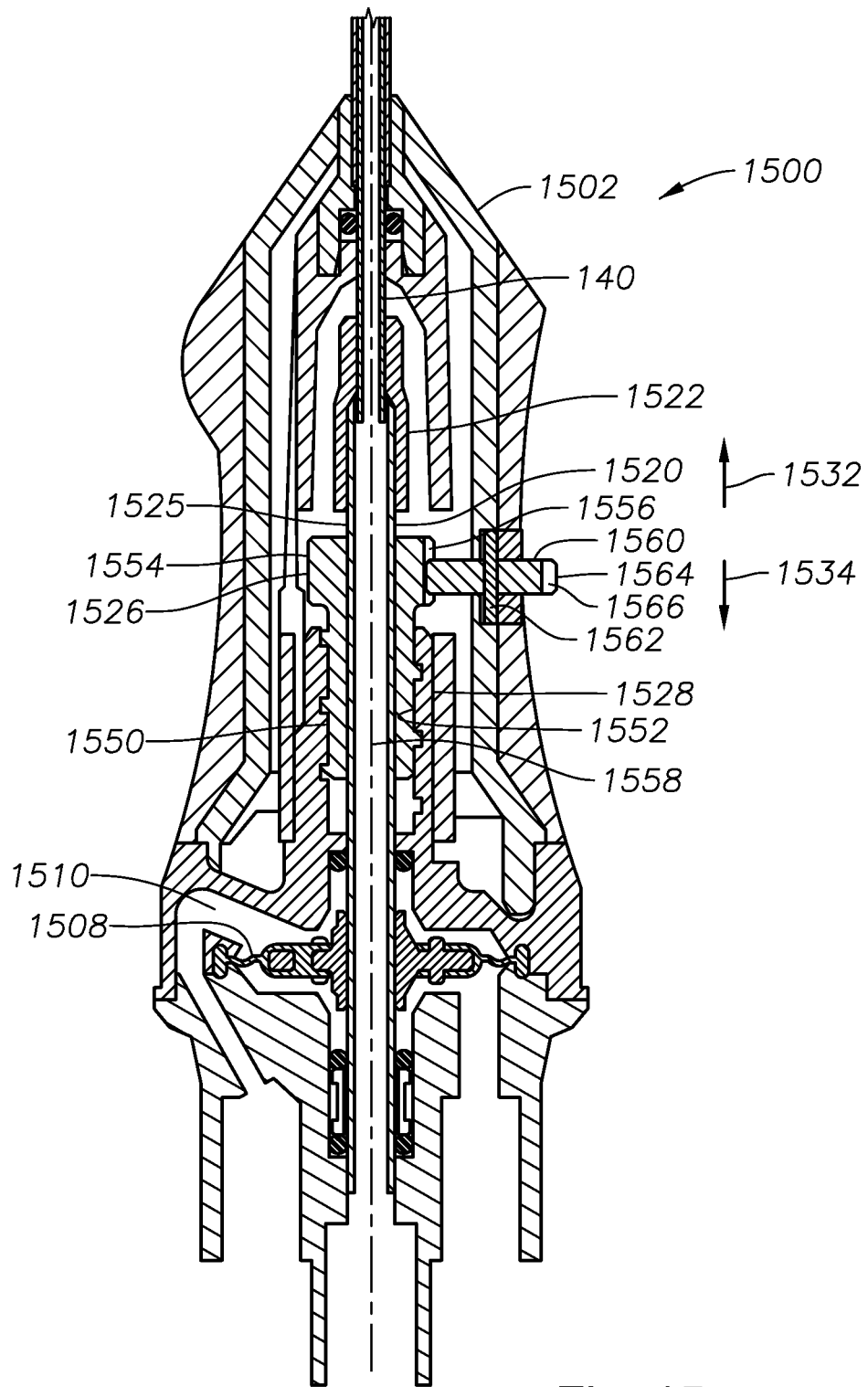
FIG. 15 is a cross-sectional view of another example vitrectomy probe including another example stroke limiting device.

FIG. 15 shows another example vitrectomy probe 1500. Probe 1500 may be similar in operation to one or more of the probes described above. For example, probe 1500 may include a housing 1502, an inner cutting member 140, coupling 1522, and a tube 1520 that, combined, form an interior assembly 1524. The interior assembly 1524 may be coupled to a diaphragm 1508 disposed in a chamber 1510. Alternating Application of pneumatic pressure to opposing sides of the diaphragm 1508 causes the diaphragm 1508 and interior assembly 1524 to oscillate.

The probe 1500 may also include a stroke limiter 1526. The stroke limiter 1526 includes a threaded surface 1550. The stroke limiter 1526 is threadably retained in an interior sleeve 1528. The interior sleeve 1528 includes an inner threaded surface 1552 that cooperatively engages the threaded surface 1550 of the stroke limiter 1526. The stroke limiter 1526 may also include a geared surface 1554. The geared surface 1554 may include a plurality of gear teeth 1556 extending in a direction parallel to a longitudinal axis 1558 of the stroke limiter 1526. A thumb screw 1560 rotatably coupled to the housing 1502 by a shaft 1562 may include a geared surface 1564 having a plurality of gear teeth 1566 also extending in a direction parallel to the longitudinal axis 1558. The plurality of gear teeth 1556 intermesh with the plurality of gear teeth 1564 such that, when the thumb screw 1560 is rotated, the stroke limiter 1526 is corresponding rotated, causing the stroke limiter 1526 to raise or lower relative to the interior sleeve 1528 as a result of the cooperatively engaging threaded surfaces 1550 and 1552. The stroke limiter 1526 and the thumb screw 1560 are configured to slide longitudinally relative to each other because of the longitudinal orientation of the intermeshing gear teeth 1556, 1566.

Consequently, a user of the probe 1500, such as a surgeon, may adjust a port size of the probe's cutter by rotating the thumb screw 1560 about shaft 1562. As explained, rotating the thumb screw 1562 in one of a first or second direction about the shaft 1562 causes the stroke limiter 1526 to one of move in a direction parallel to arrow 1532 or in a direction parallel to arrow 1534. Movement of the stroke limiter 1526 in a direction of the arrow 1532 moves the stroke limiter 1526 closer to the coupling 1522, thereby reducing the port size opening. Alternately, moving the stroke limiter 1526 in the direction of arrow 1534 increases the port size opening.

Figure 16:
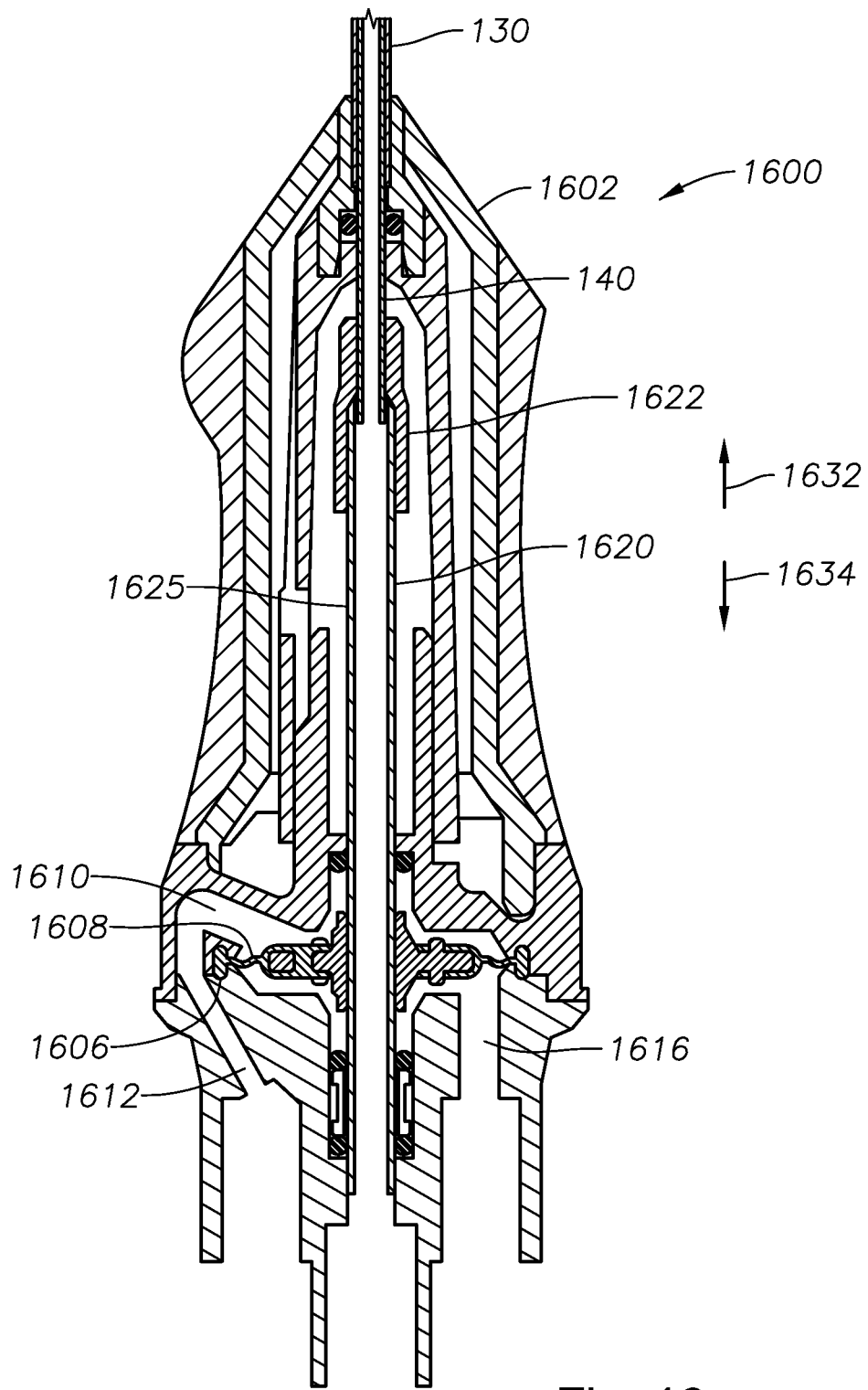
FIG. 16 is a further cross-sectional view of an example vitrectomy probe having another example user-adjusted cutter port size.

FIG. 16 shows another example variable port size vitrectomy probe 1600. Probe 1600 is similar to one or more of the probes described above in that the probe 1600 includes an outer cutting member 130, an inner cutting member 140 moveable within and relative to the outer cutting member 130. The inner cutting member 130 is coupled to coupling 1622 and tube 1620, which forms an interior assembly 1625. The tube 1620 is coupled to diaphragm 1608 fixedly coupled to housing 1602 about a periphery 1640. The diaphragm 1608 is disposed within pneumatic chamber 1610. Thus, as described above, as pneumatic pressure is alternately applied through passages 1612 and 1616 to opposite sides of the diaphragm 1608, the diaphragm and the interior assembly 1625 oscillate, resulting in the opening and closing of the cutter port.

Figure 17:
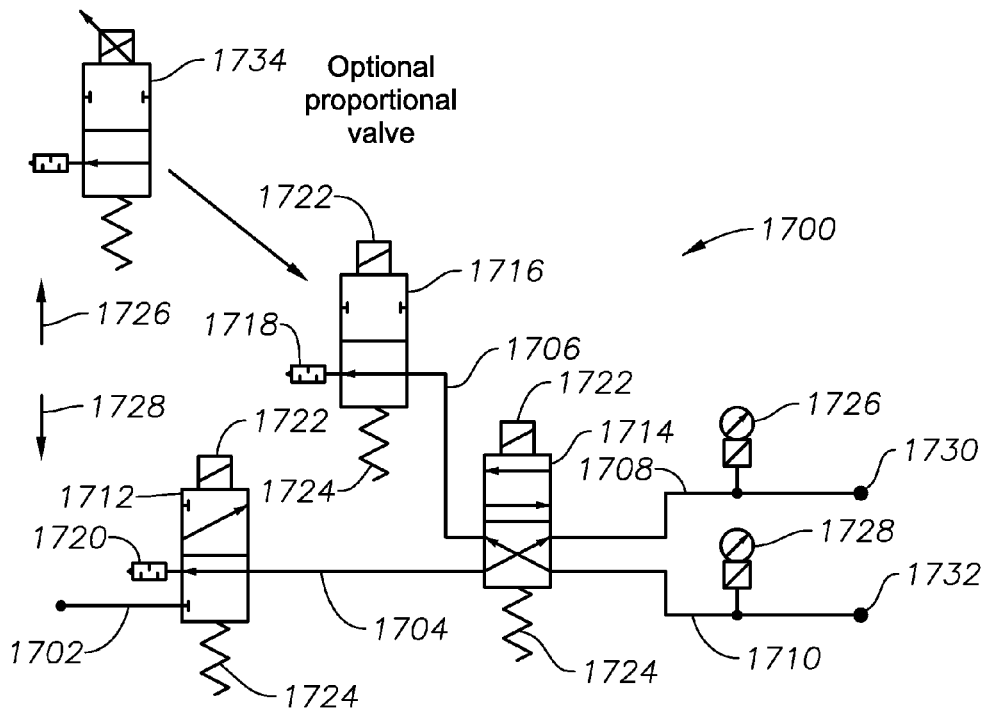
FIGS. 17-19 show example pneumatic circuits for adjusting the size of a cutter port of a vitrectomy probe.
Figure 18:
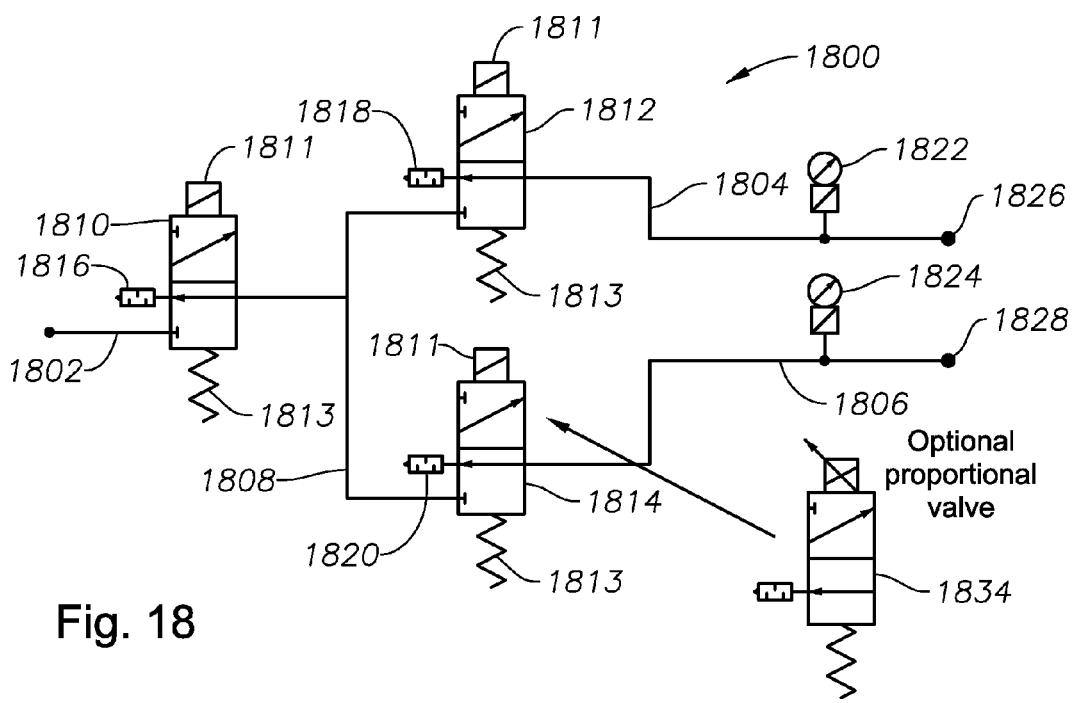
Figure 19:
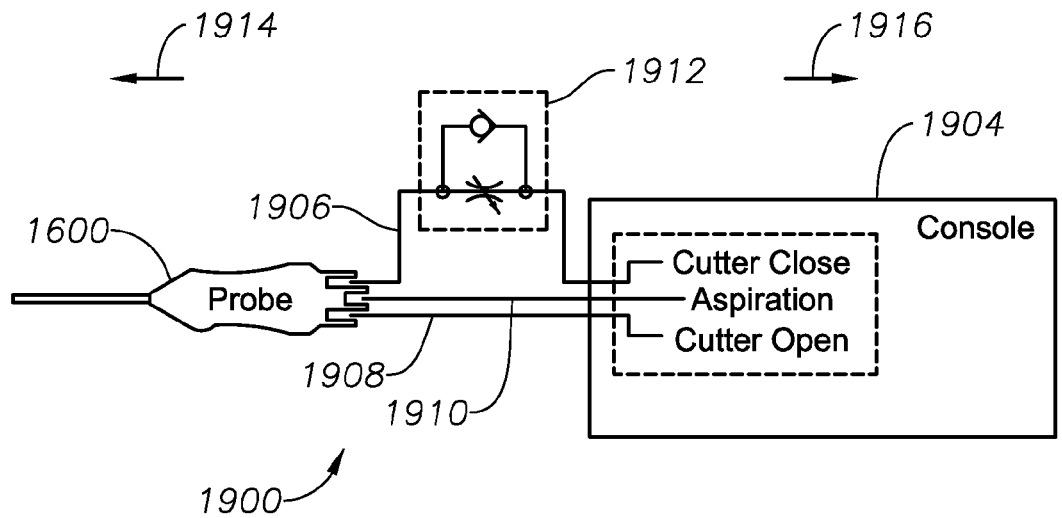

Probe 1600 may be used with any one of the example pneumatic circuits shown in FIGS. 17-19 that are utilized to control the cutting port size during operation of the probe 1600. FIG. 17 shows an example pneumatic circuit 1700. The pneumatic circuit 1700 may include pneumatic lines 1702, 1704, 1706, 1708 and 1710. An isolation valve 1712 may be disposed between pneumatic lines 1702 and 1704 and is fluidly coupled respectively thereto. An output valve 1714 is fluidly coupled to each of pneumatic lines 1704, 1706, 1708, and 1710. A venting control valve 1716 is also fluidly coupled to pneumatic line 1706. A muffler 1718 may also be fluidly coupled to the venting control valve 1716, and a muffler 1720 may be fluidly coupled to the isolation valve 1712.

Isolation valve 1712, output valve 1714, and venting control valve 1716 may be solenoid-operated valves. For example, each of valves 1712, 1714, and 1716 may include a solenoid 1722. Each of the valves 1712, 1714, and 1716 may also include a return spring 1724. Referring to the isolation valve 1712 as an example, in a rest position (shown in FIG. 17), the isolation valve 1712 fluidly communicates the pneumatic line 1704 with the muffler 1720. Consequently, in such a configuration, pneumatic pressure present in pneumatic line 1704 is vented to the atmosphere via the muffler 1720. A biasing force from return spring 1724 may bias the isolation valve 1712 in the direction of arrow 1726. Upon actuation, the solenoid 1722 moves the isolation valve 1712 in the direction of arrow 1728 and into an actuated position, compressing return spring 1724 and causing the pneumatic line 1702 to fluidly communicate with pneumatic line 1704. The pneumatic line 1702 may be a pneumatic supply line containing compressed gas. When the isolation valve 1712 is in the actuated position, the compressed gas in the pneumatic line 1702 is communicated through the isolation valve and into pneumatic line 1704. When actuation of the solenoid 1722 is ceased, the return spring 1724 returns the valve 1712 to the rest position. Output valve 1714 and venting control valve 1716 may operate in a similar manner.

In some instances, a pressure sensor 1726 may be included in pneumatic line 1708 to sense a pneumatic pressure therein. Similarly, a pressure sensor 1728 may be included in pneumatic line 1710 to sense a pneumatic pressure therein. For example, in some instances, if one or both of the pressure sensor 1726, 1728 sense a pressure outside of a selected pressure range, the pressure sensor 1726 and/or 1728 may send a signal to the console, for example, to implement a corrective action, indicate a warning to a user, cease one or more operations of the console (e.g., operation of the probe), or perform some other activity. Connectors 1730 and 1732 may be attached at ends of pneumatic lines 1708 and 1712, respectively. A vitrectomy probe, such as probe 1600, may be coupled to the connectors 1730 and 1732, such as by flexible tubing, so that passage 1612 is in fluidly communication with pneumatic line 1708 and passage 1616 is in fluid communication with pneumatic line 1710. In other implementations, these connections may be reversed.

In operation, the isolation valve 1712 may be actuated into the actuated position, thereby supplying compressed gas from the pneumatic line 1702 to the pneumatic line 1704. When the output valve 1714 is in the rest position, the pneumatic line 1704 is in communication with pneumatic line 1708, and the pneumatic line 1710 is in communication with pneumatic line 1706. Consequently, compressed gas from the pneumatic line 1704 is conducted through the output valve 1714 to the pneumatic line 1708. The compressed gas is, thus, communicated to the probe 1600 through passage 1612 and displaces the diaphragm 1608 in the direction of arrow 1634. That is, the inner cutting member 140 is retracted. Also, while the output valve 1714 is in the rest position, pneumatic pressure in the pneumatic line 1710 is allowed to pass through the output valve 1714, through pneumatic line 1706, through venting control valve 1716 (when in the rest position), and out to the environment through the muffler 1718.

When the solenoid 1722 of the output valve 1714 is actuated, the output valve 1714 moves into the actuated position, providing fluid communication between the pneumatic line 1704 and the pneumatic line 1710. Compressed gas is thus communicated through the pneumatic line 1710 and through passage 1616 of the probe 1600. The compressed gas impinges on the diaphragm 1608, causing the diaphragm 1608 to move in the direction of arrow 1632. Thus, the inner cutting member 140 is moved into the extended position. Also, pneumatic pressure in the pneumatic line 1708 is released and allowed to pass through output valve 1714, through pneumatic line 1706, through venting control valve 1722 and out to the environment through muffler 1718.

The output valve 1714 may be reciprocated to alternately supply pressurized gas to one of the pneumatic lines 1708, 1710 while releasing pneumatic pressure in the other of the pneumatic lines 1708, 1710. As a result, pneumatic pressure is alternately supplied to opposing sides of the diaphragm 1608 to cause the diaphragm 1608 and inner cutting member 140 to reciprocate. Thus, the cutter of the probe 1600 is made to operate. The output valve 1714 may be rapidly oscillated to cause the inner cutting member 140 of the probe 1600 to rapidly reciprocate.

The venting control valve 1716 may be operated to control a port size of the cutter of the probe 1600 by, for example, interrupting exhaust of pressurized gas from the passage 1616. For example, as described above, the inner cutting member 140 is retracted and the port of the cutter (see, e.g., FIGS. 4-8) is opened when the output valve 1714 is in the rest position, allowing pressurized gas to pass through pneumatic line 1708 and passage 1612 to cause the diaphragm to deflect and inner cutting member to retract in the direction of arrow 1634. At the same time, gas is allowed to pass out of the passage 1616, though pneumatic line 1710 and, ultimately, out to the environment through the venting control valve 1716 and muffler 1718. However, during a part of the time the pressurized gas is allowed to escape from passage 1616, the venting control valve 1716 may be moved to the actuated position, stopping release of the pressurized gas into the environment and, thereby, creating backpressure in the passage 1616. The generated backpressure prevents or substantially reduced further movement of the diaphragm 1608 in the direction of arrow 1634. Consequently, the amount by which the inner cutting member 140 is retracted is reduced, and, correspondingly, the port size of the cutter is reduced.

As shown in FIG. 17, a proportional valve 1734 may be used in place of the venting control valve 1716 to control a cutter port size. Rather than providing a merely an open or closed condition, the proportional valve 1734 provides an open condition that is variable. That is, the proportional valve 1734 may have a variable-sized conduit to adjust a fluid flow rate passing through the valve. For example, in some instances, the proportional valve 1734 may be a needle valve that may be placed in a closed position, preventing fluid flow, or opened to various degrees corresponding to differing fluid flow rates. Consequently, by using a proportional valve, the exhaust flow rate can be controlled. The use of a proportional valve may provide for greater control over the exhaust port size rate of change and a smooth pressure transition, as opposed to an abrupt change.

The port size of the probe's cutter may be controlled by, for example, controlling when the venting control valve 1716 is moved into the actuated position, thereby generating backpressure against movement of the diaphragm 1608. For example, the earlier the venting control valve 1716 is moved into the actuated position to generate pressure within passage 1616, the smaller the resulting cutter port size. On the other hand, the later the venting control valve 1716 is moved to the actuated position, the larger the resulting cutter port size.

Similar to the other example probes described herein, the size of the cutter opening may be adjusted by input from a user. For example, the user, such as a surgeon, may provide input to control the cutter size through an input device, such as a touch screen, a button, a knob, a slider, a footswitch, or other input device. An example footswitch may have a pivotable member actuatable by the user's foot over an angular range. As articulation of the pedal is increased, the port size of the cutter may be reduced accordingly.

FIG. 18 shows another example pneumatic circuit 1800 that may be used to control a cutter port size of a vitrectomy probe, such as probe 1600. The pneumatic circuit 1800 may include pneumatic lines 1802, 1804, and 1806 as well as a manifold 1808. Isolation valves 1810, 1812, and 1814 may also be included. The isolation valves 1810, 1812, and 1814 may be similar to the isolation valve 1712, described above. For example, each of the isolation valves 1810, 1812, and 1814 may include a solenoid actuator 1811 and a return spring 1813. Isolation valve 1810 may be fluidly coupled to the pneumatic line 1802 and manifold 1808. Isolation valve 1812 may be fluidly coupled to the pneumatic line 1804 and manifold 1808, and isolation valve 1814 may be fluidly coupled to the pneumatic line 1806 and manifold 1808. Mufflers 1816, 1818, and 1820 may be fluidly coupled to isolation valve 1810, output valve 1812, and output valve 1814, respectively. Further, pressure sensors 1822 and 1824 may be included in pneumatic lines 1804 and 1806, respectively. The pressure sensors 1822, 1824 may be similar to the pressure sensors 1726, 1728. Further, output provided by sensors may be utilized in ways similar to those described above with respect to sensors 1726, 1728. Also, the pneumatic circuit 1800 may also include connectors 1826 and 1828 to which a probe, such as probe 1600, may be coupled. For example, probe 1600 may be coupled to the connectors 1826, 1828 such that passage 1612 is in fluid communication with pneumatic line 1804 and the passage 1616 is in fluid communication with pneumatic line 1806.

In the rest position, the isolation valve 1810 provides fluid communication between the pneumatic line 1802 and the manifold 1808. Thus, with the isolation valve 1810 in the rest position, pressurized gas in the pneumatic line 1802 is communicated into the manifold 1808. In the actuated position, the manifold 1808 is placed in fluid communication with muffler 1816, and any pressurized gas in the manifold 1808 is released into the atmosphere via the muffler 1816.

In the rest position, isolation valves 1812, 1814 provide fluid communication between the pneumatic lines 1804, 1806 to the environment via mufflers 1818, 1820, respectively. In the actuated position, pressurized gas in the manifold 1808 is communicated to the respective pneumatic lines 1804, 1806. Thus, in operation, the cutter of probe 1600 may be actuated by positioning one of the isolation valves 1812 and 1814 in the rest position and the other of the isolation valves 1812 and 1814 in the actuated position. For example, the isolation valve 1812 may be positioned in the actuated position to supply pressurized gas to the diaphragm 1608, and the isolation valve 1814 may be positioned in the rest position to allow pressurized gas to escape from the passage 1616. Consequently, the diaphragm 1608 and inner cutting member 140 may be moved in the direction of arrow 1634. The positions of each isolation valve 1812, 1814 may be reversed to move the inner cutting member 140 in the opposite direction.

As also shown in FIG. 18, a proportional valve 1834, similar to the proportional valve 1734, may be used in place of one or more of the isolation valves 1812, 1814. The proportional valve 1834 may function in a similar way as the isolation valve 1734, thereby providing control over the exhaust flow rate. Consequently, the use of a proportional valve may provide for greater control over the exhaust port size rate of change and a smooth pressure transition.

The cutter port size may be controlled, for example, by controlling the time at which the isolation valve 1814 is moved from the rest position (i.e., passage 1616 open to atmosphere) to the actuated position (i.e., passage 1616 exposed to pneumatic pressure of manifold 1808) while the isolation valve 1812 is in the actuated position (i.e., passage 1612 exposed to pneumatic pressure of manifold 1808). When the isolation valve 1812 is in the actuated position and the isolation valve 1814 is in the rest position, pressurized gas is supplied from pneumatic line 1804 to the passage 1612 to move the diaphragm 1608 in the direction of arrow 1634 and pressurized gas from the passage 1616 vented to the atmosphere through pneumatic line 1806.

In other implementations, the cutter port size may be controlled by controlling an amount of time the isolation valve 1812 is placed in the actuated position and the isolation valve 1814 is placed in the rest position. For example, the amount of time the isolation valve 1812 is in the actuated position simultaneously with the isolation valve 1814 being in the rest position may be used to control the opening size of the port. Particularly, in some instances, the isolation valve 1812 may be moved into the actuated position along with the isolation valve 1814 being moved into the rest position for a shorter period of time in comparison to the isolation valve 1814 being in the actuated position and the isolation valve 1812 being in the rest position. Further, the amount of time the isolation valve 1812 is in the actuated position with the isolation valve 1814 in the rest position may be altered to control the port size. For example, a longer period of time in this configuration may result in a larger port size, while a short time period may result in a smaller port size.

In still other implementations, a manually controlled one-way restrictor vale may be placed in the pneumatic circuit, for example, between connector 1828 and the passage 1616. FIG. 19 shows an example system 1900 for operating the vitrectomy probe 1600. A vitrectomy probe, such as the vitrectomy probe 1600, is fluidly coupled to a console 1904. In some instances, the console 1904 a Constellation console and may include a controller for use in operating the vitrectomy probe 1600. A first pneumatic line 1906 and a second pneumatic line 1908 may extend between the vitrectomy probe 1600 and the console 1904. The pneumatic lines 1906, 1908 may be utilized to carry compressed gas to a motor for operating the motor 1606 of the vitrectomy probe 1600 and the cutter coupled thereto. In some instances, the pneumatic line 1906 may carry compressed gas to actuate the inner cutting member 140 so as to close the cutter port, and the pneumatic line 1908 may carry compressed gas to actuate the inner cutting member 140 so as to open the cutter port.

An aspiration line 1910 may also extend between the vitrectomy probe 1902 and the console 1904. The aspiration line 1910 may be utilized to transport materials, e.g., fluids and dissected tissues, from the probe 1902 to the console 1904. A one-way restrictor 1912 may be disposed in the pneumatic line 1906. The one-way restrictor 1912 may be operable to allow the passage of pressurized gas in a first direction 1914 with little to no resistance while providing a greater amount of resistance to flow of the pressurized gas in a second direction 1914 opposite the first direction 1902. In some instances, the amount of resistance provided by the one-way restrictor 1900 may be adjusted to control the port size. For example, a greater amount of resistance may result in a smaller port size, while a decreased amount of resistance may result in a larger port size. The amount of resistance to flow provided by the one-way restrictor 1912 may be adjusted manually, such as by a user of the probe 1600, or may be adjusted by interacting with the console 1904. For example, a user may manipulate a control of the console 1904 to adjust the restriction to air flow provided by the one-way restrictor 1912.

Figure 20:
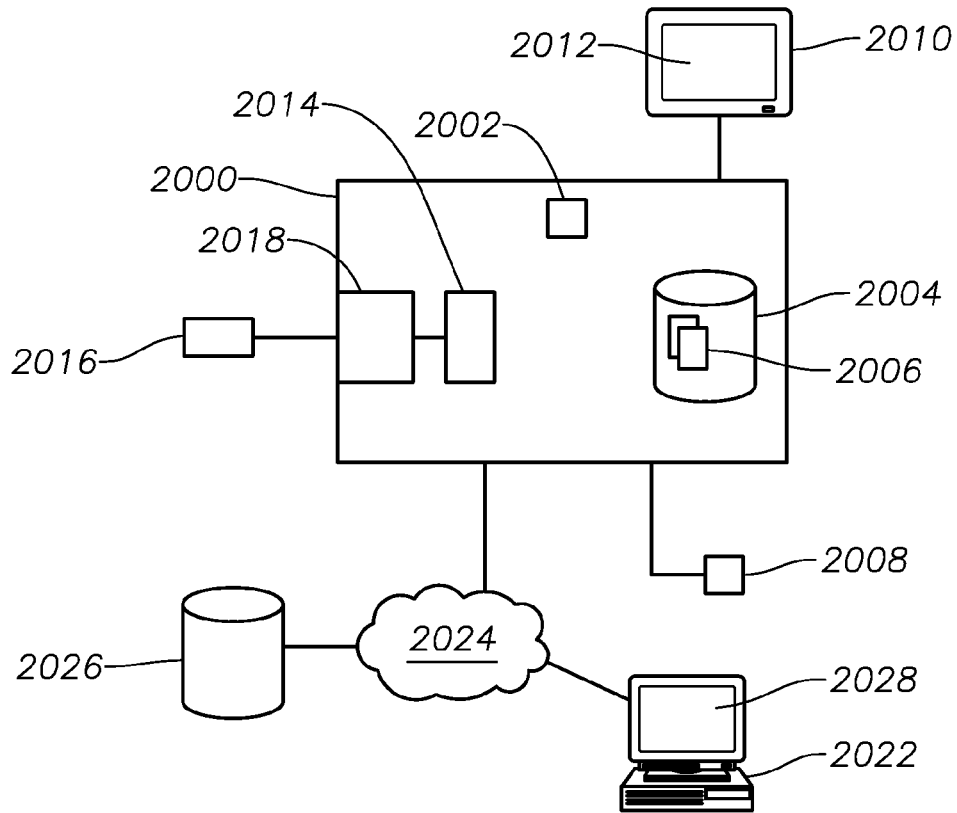
FIG. 20 is a schematic view of an example console for use with a vitrectomy probe having a user-adjustable cutter port size.

FIG. 20 shows a schematic view of an example console 2000 that may be used with one or more of the vitrectomy probes described herein. Consoles 10 and/or 1904 may be similar to the console 2000 described herein. An example vitrectomy probe 2016 is shown coupled to the console 2000. The console 2000 may be used to provide power to the probe 2016. In some instances, the power provided by the console 2000 may be pneumatic power. In other instances, the power may be electrical power. In still other instances, the power may be hydraulic power. However, in still other instances, the console 2000 may provide any suitable power to the probe 2016 for operation thereof. The console 2000 may also be operable to monitor and/or control other aspects of a surgical procedure for which the console 2000 may be used. For example, the console 2000 may be operable to control an infusion rate of fluid to a surgical site, aspiration of fluid from the surgical site, as well as to monitor one or more patient vital signs.

The console 2000 may include a processor 2002, memory 2004, and one or more applications, including vitrectomy probe application 2006. The console 2000 may also include one or more input devices 2008, and one or more output devices, such as a display 2010. The display 2010 may display a graphical user interface or application interface (collectively referred to as "GUI 2012"), discussed in more detail below. A user may interface with the GUI 2012 to interact with one or more features of the console 2000. The one or more input devices 2008 may include a keypad, a touch screen, a mouse, a foot-operated input device (e.g., a footswitch), or any other desired input device.

Additionally, the console 2000 may include an operations portion 2014. In some instances, the operations portion 2014 may include a power source for a vitrectomy probe, aspiration components, as well as one or more sensors, pumps, valves and/or other components for operating a vitrectomy probe 2016. The vitrectomy probe 2016 may be coupled to the operations portion 2014 of the console 2000 via an interface panel 2018.

Memory 2004 may include any memory or module and may take the form of volatile or non-volatile memory including, without limitation, magnetic media, optical media, random access memory (RAM), read-only memory (ROM), removable media, or any other suitable local or remote memory component. Memory 2004 may contain, among other items, the vitrectomy probe application 2006. The vitrectomy probe application 2006 may provide instructions for operating aspects of the vitrectomy probe 2016, such as the port size in the probe's 2016 cutter, cutter speed, duty cycle, cutter pulsing configuration, etc.

Memory 2004 may also store classes, frameworks, applications, backup data, jobs, or other information that includes any parameters, variables, algorithms, instructions, rules, or references thereto. Memory 2004 may also include other types of data, such as environment and/or application description data, application data for one or more applications, as well as data involving virtual private network (VPN) applications or services, firewall policies, a security or access log, print or other reporting files, HyperText Markup Language (HTML) files or templates, related or unrelated software applications or sub-systems, and others. Consequently, memory 2004 may also be considered a repository of data, such as a local data repository from one or more applications, such as vitrectomy probe application 2006. Memory 2004 may also include data that can be utilized by one or more applications, such as the vitrectomy probe application 2006.

Application 2006 may include a program or group of programs containing instructions operable to utilize received data, such as in one or more algorithms, to determine a result or output. The determined results may be used to affect an aspect of the system 2000. The application 2006 may include instructions for controlling aspects of the vitrectomy probe 2016. For example, the application 2006 may include instructions for controlling a port size of the cutter of the vitrectomy probe 2016. For example, the application 2006 may determine one or more adjustments to the operations portion 2014. The adjustments may be implemented by one or more transmitted control signals to one or more components of console 2000, such as the operations portion 2014. While an example console 2000 is shown, other implementations of the console 2000 may include more, fewer, or different components than those shown.

Processor 2002 executes instructions and manipulates data to perform the operations of the console 2000, e.g., computational and logic operations, and may be, for example, a central processing unit (CPU), a blade, an application specific integrated circuit (ASIC), or a field-programmable gate array (FPGA). Although FIG. 20 illustrates a single processor 2002 in console 2000, multiple processors 2002 may be used according to particular needs and reference to processor 2002 is meant to include multiple processors 2002 where applicable. For example, the processor 2002 may be adapted for receiving data from various components of the console 2000 and/or devices coupled thereto, process the received data, and transmit data to one or more of the components of the system 2000 and/or devices coupled thereto in response. In the illustrated embodiment, processor 2002 executes vitrectomy probe application 2006.

Further, the processor 2002 may transmit control signals to or receive signals from one or more components coupled thereto. For example, the processor 2002 may transmit control signals in response to received data. In some implementations, for example, the processor 2002 may execute the application 2006 and transmit control signals to the operations portion 2014 in response thereto.

The display 2010 displays information to a user, such as a medical practitioner. In some instances, the display 2010 may be a monitor for visually displaying information. In some instances, the display 2010 may operate both as a display and an input device. For example, the display 2010 may be a touch sensitive display in which a touch by a user or other contact with the display produces an input to the console 2000. The display 2010 may present information to the user via the GUI 2012.

GUI 2012 may include a graphical user interface operable to allow the user, such as a medical practitioner, to interface with the console 2000 for any suitable purpose, such as viewing application or other system information. For example, GUI 2012 could provide information associated with a medical procedure, including detailed information related to a vitreoretinal surgical procedure and/or operational aspects of the vitrectomy probe 2016.

Generally, GUI 2012 may provide a particular user with an efficient and user-friendly presentation of information received by, provided by, or communicated within console 2000. GUI 2012 may include a plurality of customizable frames or views having interactive fields, pull-down lists, and buttons operated by the user. GUI 2012 may also present a plurality of portals or dashboards. For example, GUI 2012 may display an interface that allows users to input and define parameters associated with the vitrectomy probe 2016. It should be understood that the term graphical user interface may be used in the singular or in the plural to describe one or more graphical user interfaces and each of the displays of a particular graphical user interface. Indeed, reference to GUI 2012 may indicate a reference to the front-end or a component of application 2006 without departing from the scope of this disclosure. Therefore, GUI 2012 contemplates any graphical user interface. For example, in some instances, the GUI 2012 may include a generic web browser for inputting data and efficiently present the results to a user. In other instances, the GUI 2012 may include a custom or customizable interface for displaying and/or interacting with the various features of the application 2006 or other system services.

In some implementations, the console 2000 may be in communication with one or more local or remote computers, such as computer 2022, over a network 2024. Network 2024 facilitates wireless or wireline communication between console 2000 and, generally, console 2000 and any other local or remote computer, such as computer 2022. For example, medical practitioners may use the computer 2022 to interact with configurations, settings, and/or other aspects associated with operation of the system 200, including the services associated with the application 2006. Network 2024 may be all or a portion of an enterprise or secured network. In another example, network 2024 may be a VPN merely between console 2000 and computer 2022 across wireline or wireless link. Such an example wireless link may be via 802.11a, 802.11b, 802.11g, 802.20, WiMax, ZigBee, Ultra-Wideband and many others. While illustrated as a single or continuous network, network 2024 may be logically divided into various sub-nets or virtual networks without departing from the scope of this disclosure, so long as at least a portion of network 2024 may facilitate communications among console 2000, computer 2022, and other devices.

For example, console 2000 may be communicably coupled to a repository 2026 through one sub-net while communicably coupled to computer 2022 through another. In other words, network 2024 encompasses any internal or external network, networks, sub-network, or combination thereof operable to facilitate communications between various computing components. Network 2024 may communicate, for example, Internet Protocol (IP) packets, Frame Relay frames, Asynchronous Transfer Mode (ATM) cells, voice, video, data, and other suitable information between network addresses (collectively or interchangeably referred to as "information"). Network 2024 may include one or more local area networks (LANs), radio access networks (RANs), metropolitan area networks (MANs), wide area networks (WANs), all or a portion of the global computer network known as the Internet, and/or any other communication system or systems at one or more locations. In certain embodiments, network 2024 may be a secure network accessible to users via certain local or remote computer 2022.

Computer 2022 may be any computing device operable to connect or communicate with console 2000 or network 2024 using any communication link. In some instances, computer 2022 may include an electronic computing device operable to receive, transmit, process, and store any appropriate data associated with console 2000. Computer 2022 may also include or execute a GUI 2028. GUI 2028 may similar to GUI 2012. It will be understood that there may be any number of computers 2022 communicably coupled to console 2000. Moreover, for ease of illustration, computer 2022 is described in terms of being used by one user. But this disclosure contemplates that many users may use one computer or that one user may use multiple computers.

As used in this disclosure, computer 2022 is intended to encompass a personal computer, touch screen terminal, workstation, network computer, kiosk, wireless data port, smart phone, personal data assistant (PDA), one or more processors within these or other devices, or any other suitable processing device. For example, computer 2022 may be a PDA operable to wirelessly connect with an external or unsecured network. In another example, computer 2022 may be a laptop computer that includes an input device, such as a keypad, touch screen, mouse, or other device that can accept information, and an output device that conveys information associated with the operation of console 2000 or computer 2022, including digital data, visual information, or user interface, such as GUI 2028. Both input devices and output devices may include fixed or removable storage media such as a magnetic computer disk, CD-ROM, or other suitable media to both receive input from and provide output to users of computer 2022 through, for example, a display.

As explained above, application 2006 may include instructions for controlling aspects of the vitrectomy probe 2016. Example aspects may include cutter speed, cutter port size, cutter duty cycle, as well as others. Thus, the console 2000 may be operable to control the port size of the example vitrectomy probe 2016. In controlling the vitrectomy port size, a user may indicate a desired port opening size with an input via an input device. For example, the cutter port size may be adjusted via the input device 2008.

In instances in which the vitrectomy probe 2016 includes a piezoelectric motor, such as a piezoelectric motor similar to the piezoelectric motor 926 described above, a user may adjust the cutter port size via the input device 2008. In response, the console may output a signal to the piezoelectric motor to effect the desired port size. For example, if an increased port size is indicated, the console 2000 may output an AC current to alter a position of a lead screw thereof to increase the port size. If a decreased port size is indicated, the console 2000 may output an AC current to alter the lead screw position to decrease the port size.

In some instances, the application 2006 may include instructions for controlling the port size of a vitrectomy probe with an SMA element, which may be similar to SMA element 1026. Accordingly, a user input to adjust the port size of vitrectomy probe 2016 may cause the controller 2000 to output electrical power to cause the SMA element to adjust the port size to the desired level. For example, in some example implementations, when an increased port size is desired, the console 2000 may decrease or stop output of electrical power to the SMA element to cause an increased port size. Alternately, if a decreased port size is desired, the console 2000 may increase electrical power to decrease the port size.

In other instances, the vitrectomy probe 2016 may include a stroke limiter similar to the stroke limiter 1126, described above. Accordingly, when a user indicates a change in port size, e.g., via an input device, the controller 2000 may output or alter an output of power to cause the stroke limiter to alter the port size accordingly. For example, where a port size change is indicated, the console 2000 may adjust an electrical voltage to the stroke limiter to adjust the port size accordingly.

In other instances where example vitrectomy probe 2016 is similar to vitrectomy probe 1200, the console 2000 may alter port size, for example, by altering a pneumatic pressure supplied to the probe 2016. For example, where a decreased port size is indicated by the user, the console 2000 may increase a pneumatic pressure supplied to the probe 2016. Alternately, where an increased port size is indicated, the console 2000 may respond by decreasing a pneumatic pressure supplied to the probe 2016.

In instances in which the vitrectomy probe 2016 is similar to probe 1300, the port size may also be adjusted by altering a pneumatic pressure supplied to a pneumatic chamber similar to second chamber 1360. Where a decreased port size is indicated, the console 2000 may increase a pneumatic pressure supplied to the pneumatic chamber. Where an increased port size is indicated, a decreased pneumatic pressure may be supplied to the pneumatic chamber.

For a vitrectomy probe similar to vitrectomy probe 1600, the console may adjust the port size such as by operating the pneumatic circuits 1700, 1800, and 1900 as described in detail above.

While examples are provided above, they are provided merely as examples and are not intended to limit the scope of the present disclosure.

In some implementations, the input device 2008 may be a footswitch coupled to the console 2000, such as via a wired or wireless connection. A surgeon may adjust the port size by manipulating a control on the footswitch. For example, the footswitch may include a pedal pivotable within a range, and the surgeon may adjust the port size by actuating the pedal within the range. The footswitch may also include other controls, such as one or more buttons, for example, to adjust a cutting rate (e.g., the rate at which the inner cutting member 130 is reciprocated), an aspiration rate (e.g., an amount of suction applied through the vitrectomy probe), and a duty cycle. Any of these aspects of the vitrectomy probe may be altered independently of the others.

It should be understood that, although many aspects have been described herein, some implementations may include all of the features, while others may include some features while omitting others. That is, various implementations may include one, some, or all of the features described herein.

A number of implementations have been described. Nevertheless, it will be understood that various modifications may be made without departing from the spirit and scope of the disclosure. Accordingly, other implementations are within the scope of the following claims.

What is claimed is:

1. A system for performing a vitrectomy comprising:
   a vitrectomy probe comprising:
      a first inlet port operable to conduct pneumatic pressure to an oscillator;
      a second inlet port operable to conduct pneumatic pressure to the oscillator; and
      a cutter comprising a first portion and a second portion, the oscillator operable to reciprocate the first portion relative to the second portion, an amount of movement of the first portion relative to the second portion defining a port size of the cutter;
   a control system comprising:
      an output valve;
      a first output port operable to provide communication between the first inlet port of the vitrectomy probe and the output valve;
      a second output port operable to provide communication between the second inlet port of the vitrectomy probe and the output valve;
      a first conduit coupled to the output valve and operable to provide communication with the output valve;
      a venting control valve;
      a second conduit extending between the output valve and the venting control valve operable to conduct pneumatic pressure from the output valve to the venting control valve;
      a first outlet coupled to the venting control valve and open to the atmosphere, the venting control valve operable to selectively vent pneumatic pressure from the second conduit to the atmosphere; and a controller operable to:
oscillate the output valve between a first position in which pneumatic pressure is communicated from the first conduit to the first output port and pneumatic pressure is communicated from the second output port to the second conduit, and a second position in which pneumatic pressure is communicated from the first conduit to the second output port and pneumatic pressure is communicated from the first output port to the second conduit, the output valve maintained at the first position and the second position for a selected time period; and
move the venting control valve between a first position in which a first amount of pneumatic pressure from the second conduit is vented to the atmosphere through the first outlet and a second position in which a second amount of pneumatic pressure is vented to the atmosphere through the first outlet, the controller operable to maintain the venting control valve at the first position for a first period of time less than the selected period of time when the output valve is in the second position and move the venting control valve from the first position to the second position after the first period of time has elapsed to define the port size of the vitrectomy probe.

2. The system of claim 1, wherein the first amount of pneumatic pressure is greater than the second amount of pneumatic pressure.

3. The control system of claim 1, wherein the venting control valve is an on/off valve,
wherein the first position of the venting control valve is a fully open position, and
wherein the second position of the venting control valve is a fully closed position.

4. The control system of claim 1, wherein the venting control valve is a proportional valve,
wherein the first amount of pneumatic pressure vented to the atmosphere comprises a first variable amount of communication, and
wherein the second amount of communication between the second conduit and the second outlet when the venting control valve is in the second position comprises a second variable amount of communication between the second conduit and the second outlet, the first variable amount of communication being different than the second variable amount of communication.

5. The control system of claim 4, wherein the first variable amount of communication is greater than the second variable amount of communication.

6. The system of claim 1, wherein the control system further comprises:
an isolation valve, the first conduit extending between the isolation valve and the output valve;
an inlet conduit coupled to the isolation valve and operable to communicate pneumatic pressure to the isolation valve,
a second outlet coupled to the isolation valve and open to the atmosphere;
wherein the controller is further operable to move the isolation valve between a first position in which the inlet conduit is in communication with the second outlet to vent pneumatic pressure in the first outlet conduit to the atmosphere and a second position in which the inlet conduit is in communication with the first conduit to conduct pneumatic pressure to the output valve.

7. The system of claim 1, wherein the control system further comprises:
a first pressure sensor coupled to the first output port; and
a second pressure sensor coupled to the second output port, wherein controller is operable to:
receive a first signal from the first pressure sensor corresponding to pneumatic pressure at the first output port and a second signal from the second pressure sensor corresponding to pneumatic pressure at the second output port; and
move the isolation valve to the first position if the first pressure signal or the second pressure signal is outside of a selected range.

* * * * *